United States Patent
Gifford, III et al.

(10) Patent No.: US 11,039,813 B2
(45) Date of Patent: Jun. 22, 2021

(54) DEVICES AND METHODS FOR MEASUREMENT OF VENA CAVA DIMENSIONS, PRESSURE AND OXYGEN SATURATION

(71) Applicant: Foundry Innovation & Research 1, Ltd., Dublin (IE)

(72) Inventors: Hanson S. Gifford, III, Woodside, CA (US); Mark E. Deem, Mountain View, CA (US); Martin L. Mayse, Wayzata, MN (US); Vijaykumar Rajasekhar, San Francisco, CA (US)

(73) Assignee: Foundry Innovation & Research 1, Ltd., Dublin (IE)

( * ) Notice: Subject to any disclaimer, the term of this patent is extended or adjusted under 35 U.S.C. 154(b) by 422 days.

(21) Appl. No.: 15/750,100

(22) PCT Filed: Aug. 3, 2016

(86) PCT No.: PCT/US2016/045385
§ 371 (c)(1),
(2) Date: Feb. 2, 2018

(87) PCT Pub. No.: WO2017/024051
PCT Pub. Date: Feb. 9, 2017

(65) Prior Publication Data
US 2018/0220992 A1    Aug. 9, 2018

Related U.S. Application Data

(60) Provisional application No. 62/294,986, filed on Feb. 12, 2016, provisional application No. 62/200,409, filed on Aug. 3, 2015.

(51) Int. Cl.
*A61B 8/00*    (2006.01)
*A61B 8/08*    (2006.01)
(Continued)

(52) U.S. Cl.
CPC .......... *A61B 8/445* (2013.01); *A61B 5/1076* (2013.01); *A61B 5/6855* (2013.01);
(Continued)

(58) Field of Classification Search
CPC ... A61B 5/6855; A61B 5/6859; A61B 8/4272; A61B 8/04; A61B 5/1076; A61B 8/0891;
(Continued)

(56) References Cited

U.S. PATENT DOCUMENTS

| 3,568,661 A | 3/1971 | Franklin |
| 4,142,412 A | 3/1979 | McLeod |

(Continued)

FOREIGN PATENT DOCUMENTS

| DE | 102005035022 A1 | 11/2006 |
| EP | 0399059 A1 | 5/1989 |

(Continued)

OTHER PUBLICATIONS

International Search Report and Written Opinion dated Oct. 19, 2017, in connection with PCT/US2017/046204.
(Continued)

*Primary Examiner* — Eric J Messersmith
(74) *Attorney, Agent, or Firm* — Downs Rachlin Martin PLLC

(57) ABSTRACT

Catheter-based devices and methods for continuously monitoring vascular lumen dimensions, in particular in the inferior vena cava (IVC) for determining heart failure and/or fluid status of a patient. Related therapy systems and methods for integrated monitoring and therapy are also disclosed.

14 Claims, 15 Drawing Sheets

(51) Int. Cl.
  *A61B 8/12* (2006.01)
  *A61B 8/06* (2006.01)
  *A61B 5/00* (2006.01)
  *A61B 5/107* (2006.01)
  *A61M 25/04* (2006.01)
  *A61B 8/04* (2006.01)

(52) U.S. Cl.
  CPC .......... *A61B 5/6859* (2013.01); *A61B 5/6882* (2013.01); *A61B 8/04* (2013.01); *A61B 8/06* (2013.01); *A61B 8/0891* (2013.01); *A61B 8/12* (2013.01); *A61B 8/4272* (2013.01); *A61B 8/5223* (2013.01); *A61M 25/04* (2013.01); *A61B 8/0858* (2013.01); *A61B 8/4477* (2013.01); *A61B 8/488* (2013.01)

(58) Field of Classification Search
  CPC .......... A61B 8/06; A61B 8/5223; A61B 8/12; A61B 8/445; A61B 5/6882; G16H 50/30; A61M 25/04
  USPC .......................................................... 600/481
  See application file for complete search history.

(56) References Cited

U.S. PATENT DOCUMENTS

| | | | |
|---|---|---|---|
| RE32,361 | E | 2/1987 | Duggan |
| 4,926,875 | A | 5/1990 | Rabinovitz et al. |
| 4,947,852 | A | 8/1990 | Nassi et al. |
| 5,127,404 | A | 7/1992 | Wyborny et al. |
| 5,205,292 | A | 4/1993 | Czar et al. |
| 5,316,001 | A | 5/1994 | Ferek-Petric et al. |
| 5,339,816 | A | 8/1994 | Akamatsu et al. |
| 5,495,852 | A | 3/1996 | Stadler et al. |
| 5,630,836 | A | 5/1997 | Prem et al. |
| 5,752,522 | A | 5/1998 | Murphy |
| 5,872,520 | A | 2/1999 | Siefert et al. |
| 5,902,308 | A | 5/1999 | Murphy |
| 5,967,986 | A | 10/1999 | Cimochowski |
| 6,010,511 | A | 1/2000 | Murphy |
| 6,012,457 | A | 1/2000 | Lesh |
| 6,015,386 | A | 1/2000 | Kensey et al. |
| 6,025,725 | A | 2/2000 | Gershenfeld et al. |
| 6,039,701 | A | 3/2000 | Sliwa et al. |
| 6,053,873 | A | 4/2000 | Govari et al. |
| 6,111,520 | A | 8/2000 | Allen et al. |
| 6,115,633 | A | 9/2000 | Lang et al. |
| 6,115,636 | A | 9/2000 | Ryan |
| 6,164,283 | A | 12/2000 | Lesh |
| 6,206,835 | B1 | 3/2001 | Spillman, Jr. et al. |
| 6,231,516 | B1 | 5/2001 | Keilman et al. |
| 6,261,233 | B1 | 7/2001 | Kantorovich |
| 6,278,379 | B1 | 8/2001 | Allen et al. |
| 6,287,253 | B1 | 9/2001 | Ortega et al. |
| 6,325,762 | B1 | 12/2001 | Tjin |
| 6,339,816 | B1 | 1/2002 | Bausch |
| 6,354,999 | B1 | 3/2002 | Dgany et al. |
| 6,398,734 | B1 | 6/2002 | Cimochowski et al. |
| 6,434,411 | B1 | 8/2002 | Duret |
| 6,503,202 | B1 | 1/2003 | Hossack et al. |
| 6,574,510 | B2 | 6/2003 | Von Arx et al. |
| 6,673,020 | B2 | 1/2004 | Okada et al. |
| 6,699,186 | B1 | 3/2004 | Wolinsky et al. |
| 6,738,671 | B2 | 5/2004 | Christophersom et al. |
| 6,802,811 | B1 | 10/2004 | Slepian |
| 6,855,115 | B2 | 2/2005 | Fonseca et al. |
| 6,926,670 | B2 | 8/2005 | Rich et al. |
| 6,972,553 | B2 | 12/2005 | Petrovich et al. |
| 7,065,409 | B2 | 6/2006 | Mazar |
| 7,077,812 | B2 | 7/2006 | Naghavi |
| 7,082,330 | B2 | 7/2006 | Stadler et al. |
| 7,147,604 | B1 | 12/2006 | Allen et al. |
| 7,149,587 | B2 | 12/2006 | Wardle et al. |
| 7,191,013 | B1 | 3/2007 | Miranda et al. |
| 7,225,032 | B2 | 5/2007 | Schmeling et al. |
| 7,233,821 | B2 | 6/2007 | Hettrick et al. |
| 7,236,821 | B2 | 6/2007 | Cates et al. |
| 7,245,117 | B1 | 7/2007 | Joy |
| 7,284,442 | B2 | 10/2007 | Fleischman et al. |
| 7,367,984 | B2 | 5/2008 | Kulcinski et al. |
| 7,423,496 | B2 | 9/2008 | Scheuermann |
| 7,432,723 | B2 | 10/2008 | Ellis |
| 7,439,723 | B2 | 10/2008 | Allen |
| 7,444,878 | B1 | 11/2008 | Pepples |
| 7,452,334 | B2 | 11/2008 | Gianchandani et al. |
| 7,454,244 | B2 | 11/2008 | Kassab et al. |
| 7,466,120 | B2 | 12/2008 | Miller |
| 7,479,112 | B2 | 1/2009 | Sweeney et al. |
| 7,481,771 | B2 | 1/2009 | Fonseca |
| 7,492,144 | B2 | 2/2009 | Powers et al. |
| 7,498,799 | B2 | 3/2009 | Allen |
| 7,550,978 | B2 | 6/2009 | Joy |
| 7,574,792 | B2 | 8/2009 | O'Brien |
| 7,595,647 | B2 | 9/2009 | Kroh |
| 7,618,363 | B2 | 11/2009 | Yadav |
| 7,621,036 | B2 | 11/2009 | Cros |
| 7,621,876 | B2 | 11/2009 | Hoctor et al. |
| 7,647,831 | B2 | 1/2010 | Corcoran |
| 7,647,836 | B2 | 1/2010 | O'Brien |
| 7,662,653 | B2 | 2/2010 | O'Brien |
| 7,667,547 | B2 | 2/2010 | Ellis |
| 7,677,107 | B2 | 3/2010 | Nunez |
| 7,678,135 | B2 | 3/2010 | Maahs et al. |
| 7,679,355 | B2 | 3/2010 | Allen |
| 7,699,059 | B2 | 4/2010 | Fonseca et al. |
| 7,710,103 | B2 | 5/2010 | Powers |
| 7,725,160 | B2 | 5/2010 | Weber |
| 7,748,277 | B2 | 7/2010 | O'Brien |
| 7,778,684 | B2 | 8/2010 | Weber et al. |
| 7,786,867 | B2 | 8/2010 | Hamel et al. |
| 7,812,416 | B2 | 10/2010 | Courcimault |
| 7,829,363 | B2 | 11/2010 | You |
| 7,839,153 | B2 | 11/2010 | Joy |
| 7,848,813 | B2 | 12/2010 | Bergelson et al. |
| 7,854,172 | B2 | 12/2010 | O'Brien |
| 7,908,002 | B2 | 3/2011 | Hoijer |
| 7,908,018 | B2 | 3/2011 | O'Brien |
| 7,909,770 | B2 | 3/2011 | Stern et al. |
| 7,932,732 | B2 | 4/2011 | Ellis |
| 7,936,174 | B2 | 5/2011 | Ellis |
| 7,955,269 | B2 | 6/2011 | Stahmann |
| 7,966,886 | B2 | 6/2011 | Corcoran et al. |
| 7,988,719 | B2 | 8/2011 | Alt et al. |
| 8,016,766 | B2 | 9/2011 | Goedje et al. |
| 8,021,307 | B2 | 9/2011 | White |
| 8,025,625 | B2 | 9/2011 | Allen |
| 8,026,729 | B2 | 9/2011 | Kroh |
| 8,060,214 | B2 | 11/2011 | Larson et al. |
| 8,078,274 | B2 | 12/2011 | Kassab |
| 8,082,032 | B2 | 12/2011 | Kassab et al. |
| 8,099,161 | B2 | 1/2012 | Kassab |
| 8,107,248 | B2 | 1/2012 | Shin et al. |
| 8,111,150 | B2 | 2/2012 | Miller |
| 8,114,143 | B2 | 2/2012 | Kassab et al. |
| 8,118,749 | B2 | 2/2012 | White |
| 8,154,389 | B2 | 4/2012 | Rowland |
| 8,159,348 | B2 | 4/2012 | Ellis |
| 8,185,194 | B2 | 5/2012 | Kassab |
| 8,209,033 | B2 | 6/2012 | Zhang et al. |
| 8,221,405 | B2 | 7/2012 | Whisenant et al. |
| 8,237,451 | B2 | 8/2012 | Joy |
| 8,264,240 | B2 | 9/2012 | Park et al. |
| 8,267,954 | B2 | 9/2012 | Decant, Jr. et al. |
| 8,278,941 | B2 | 10/2012 | Kroh |
| 8,298,147 | B2 | 10/2012 | Huennekens et al. |
| 8,298,148 | B2 | 10/2012 | Furman |
| 8,353,841 | B2 | 1/2013 | White |
| 8,355,777 | B2 | 1/2013 | White |
| 8,356,399 | B2 | 1/2013 | Kaplan |
| 8,360,984 | B2 | 1/2013 | Yadav |
| 8,374,689 | B2 | 2/2013 | Gopinathan et al. |
| 8,432,265 | B2 | 4/2013 | Rowland |
| 8,442,639 | B2 | 5/2013 | Walker et al. |

(56) References Cited

U.S. PATENT DOCUMENTS

| | | |
|---|---|---|
| 8,465,436 B2 | 6/2013 | Griswold |
| 8,465,452 B2 | 6/2013 | Kassab |
| 8,467,854 B2 | 6/2013 | Lewis et al. |
| 8,493,187 B2 | 7/2013 | Rowland |
| 8,500,660 B2 | 8/2013 | Buchwald et al. |
| 8,521,282 B2 | 8/2013 | Czygan et al. |
| 8,527,046 B2 | 9/2013 | Connelly et al. |
| 8,556,929 B2 | 10/2013 | Harper et al. |
| 8,570,186 B2 | 10/2013 | Nagy |
| 8,600,517 B2 | 12/2013 | Forsell |
| 8,613,705 B2 | 12/2013 | Scheurer et al. |
| 8,632,469 B2 | 1/2014 | Kassab |
| 8,644,941 B2 | 2/2014 | Rooney et al. |
| 8,665,086 B2 | 3/2014 | Miller et al. |
| 8,669,770 B2 | 3/2014 | Cros |
| 8,696,584 B2 | 4/2014 | Kassab |
| 8,702,613 B2 | 4/2014 | Kassab |
| 8,706,208 B2 | 4/2014 | Chiao et al. |
| 8,706,209 B2 | 4/2014 | Kassab |
| 8,728,012 B2 | 5/2014 | Braido |
| 8,784,338 B2 | 7/2014 | Wallace |
| 8,798,712 B2 | 8/2014 | Gopinathan et al. |
| 8,814,798 B2 | 8/2014 | Corbucci et al. |
| 8,818,507 B2 | 8/2014 | Liu et al. |
| 8,825,151 B2 | 9/2014 | Gopinathan et al. |
| 8,827,929 B2 | 9/2014 | O'Dea |
| 8,855,783 B2 | 10/2014 | Dagan et al. |
| 8,864,666 B2 | 10/2014 | Kassem |
| 8,870,787 B2 | 10/2014 | Yadav |
| 8,874,203 B2 | 10/2014 | Kassab et al. |
| 8,886,301 B2 | 11/2014 | Kassab |
| 8,894,582 B2 | 11/2014 | Nunez |
| 8,896,324 B2 | 11/2014 | Kroh |
| 8,909,351 B2 | 12/2014 | Dinsmoor et al. |
| 8,918,169 B2 | 12/2014 | Kassab et al. |
| 8,938,292 B2 | 1/2015 | Hettrick et al. |
| 8,951,219 B2 | 2/2015 | Gerber et al. |
| 9,049,995 B2 | 6/2015 | Blomqvist et al. |
| 9,060,798 B2 | 6/2015 | Harper et al. |
| 9,061,099 B2 | 6/2015 | Gerber et al. |
| 9,066,672 B2 | 6/2015 | Kassab et al. |
| 9,198,706 B2 | 12/2015 | Kassab et al. |
| 9,265,428 B2 | 2/2016 | O'Brien et al. |
| 9,289,132 B2 | 3/2016 | Ghaffari et al. |
| 9,289,229 B2 | 3/2016 | Kassab |
| 9,305,456 B2 | 4/2016 | Rowland |
| 9,314,169 B2 | 4/2016 | Kassab |
| 9,326,728 B2 | 5/2016 | Demir et al. |
| 9,332,914 B2 | 5/2016 | Langston |
| 9,332,916 B2 | 5/2016 | Kassab |
| 9,333,365 B2 | 5/2016 | Zhao |
| 9,351,661 B2 | 5/2016 | Kassab |
| 9,393,416 B2 | 7/2016 | Rooney et al. |
| 9,445,743 B2 | 9/2016 | Kassab |
| 9,489,831 B2 | 11/2016 | Nagy et al. |
| 9,526,637 B2 | 12/2016 | Dagan et al. |
| 9,603,533 B2 | 3/2017 | Lading et al. |
| 9,662,066 B2 | 5/2017 | Ledet et al. |
| 9,675,257 B2 | 6/2017 | Kassab |
| 9,675,315 B2 | 6/2017 | Song et al. |
| 9,721,463 B2 | 8/2017 | Rowland |
| 9,814,395 B2 | 11/2017 | Stahmann et al. |
| 9,878,080 B2 | 1/2018 | Kaiser et al. |
| 9,901,722 B2 | 2/2018 | Nitzan et al. |
| 9,996,712 B2 | 6/2018 | Sundaram et al. |
| 10,080,528 B2 | 9/2018 | BeBusschere et al. |
| 10,092,247 B2 | 10/2018 | Taylor |
| 10,105,103 B2 | 10/2018 | Goldshtein et al. |
| 10,194,808 B1 | 2/2019 | Thompson |
| 10,195,441 B2 | 2/2019 | Kaiser |
| 10,201,285 B2 | 2/2019 | Sawanoi |
| 10,210,956 B2 | 2/2019 | Lavi |
| 10,213,129 B2 | 2/2019 | Kassab |
| 10,219,704 B2 | 3/2019 | Lavi |
| 10,219,720 B2 | 3/2019 | Kassab |
| 10,219,724 B2 | 3/2019 | Stern |
| 10,226,203 B2 | 3/2019 | Stigall |
| 10,226,218 B2 | 3/2019 | Rowland |
| 10,231,659 B2 | 3/2019 | Vanslyke |
| 10,231,701 B2 | 3/2019 | Ryan |
| 10,236,084 B2 | 3/2019 | Grady |
| 10,238,311 B2 | 3/2019 | Kassab |
| 10,238,322 B2 | 3/2019 | Vanslyke |
| 10,238,323 B2 | 3/2019 | Vanslyke |
| 10,238,324 B2 | 3/2019 | Vanslyke |
| 10,240,994 B1 | 3/2019 | Xu |
| 10,265,024 B2 | 4/2019 | Lee |
| 10,271,797 B2 | 4/2019 | Zhang |
| 10,537,281 B2 | 1/2020 | Thompson et al. |
| 10,542,887 B2 | 1/2020 | Sarkar et al. |
| 10,660,577 B2 | 1/2020 | Thakur et al. |
| 10,548,535 B2 | 2/2020 | Zhang et al. |
| 10,555,704 B2 | 2/2020 | Averina et al. |
| 10,582,866 B2 | 3/2020 | Badie et al. |
| 10,588,528 B2 | 3/2020 | Banet et al. |
| 10,595,734 B2 | 3/2020 | Thakur et al. |
| 10,596,381 B2 | 3/2020 | Averina et al. |
| 10,638,980 B2 | 5/2020 | Gyllensten et al. |
| 10,687,715 B2 | 6/2020 | Jansen et al. |
| 10,702,213 B2 | 7/2020 | Sharma et al. |
| 2002/0120205 A1 | 8/2002 | Ferek-Petric |
| 2003/0037591 A1 | 2/2003 | Ashton et al. |
| 2003/0100940 A1 | 5/2003 | Yodfat |
| 2003/0158584 A1 | 8/2003 | Cates et al. |
| 2004/0106871 A1 | 6/2004 | Hunyor et al. |
| 2004/0116992 A1 | 6/2004 | Wardle |
| 2004/0133092 A1 | 7/2004 | Kain |
| 2004/0140939 A1 | 7/2004 | Haller et al. |
| 2004/0167596 A1 | 8/2004 | Richter |
| 2004/0215235 A1 | 10/2004 | Jackson et al. |
| 2005/0148903 A1 | 7/2005 | Diamantopoulos |
| 2005/0154321 A1 | 7/2005 | Wolinsky |
| 2006/0056161 A1 | 3/2006 | Shin |
| 2006/0106321 A1 | 5/2006 | Lewinsky et al. |
| 2006/0122522 A1 | 6/2006 | Chavan et al. |
| 2006/0149166 A1* | 7/2006 | Zvuloni ............... A61B 17/22 600/587 |
| 2006/0174712 A1 | 8/2006 | O'Brien |
| 2006/0177956 A1 | 8/2006 | O'Brien |
| 2006/0178695 A1 | 8/2006 | Decant |
| 2006/0253160 A1 | 11/2006 | Benditt et al. |
| 2006/0271119 A1 | 11/2006 | Ni et al. |
| 2006/0287602 A1 | 12/2006 | Obrien et al. |
| 2006/0287700 A1 | 12/2006 | White |
| 2007/0088214 A1 | 4/2007 | Shuros et al. |
| 2007/0129637 A1 | 6/2007 | Wolinsky et al. |
| 2007/0158769 A1 | 7/2007 | You |
| 2007/0199385 A1 | 8/2007 | O'Brien |
| 2007/0274565 A1 | 11/2007 | Penner |
| 2007/0282210 A1 | 12/2007 | Stern |
| 2007/0292090 A1* | 12/2007 | Alphonse ............ A61B 5/02007 385/119 |
| 2008/0015569 A1* | 1/2008 | Saadat ................. A61B 5/6882 606/41 |
| 2008/0033527 A1 | 2/2008 | Nunez et al. |
| 2008/0077016 A1 | 3/2008 | Sparks |
| 2008/0097227 A1 | 4/2008 | Zdeblick et al. |
| 2008/0177186 A1 | 7/2008 | Slater et al. |
| 2008/0294041 A1 | 11/2008 | Kassab |
| 2009/0007679 A1 | 1/2009 | Nunez |
| 2009/0009332 A1 | 1/2009 | Nunez |
| 2009/0011117 A1 | 1/2009 | Nunez |
| 2009/0024042 A1 | 1/2009 | Nunez |
| 2009/0030291 A1 | 1/2009 | O'Brien |
| 2009/0062684 A1 | 3/2009 | Gregersen et al. |
| 2009/0105799 A1 | 4/2009 | Hekmat et al. |
| 2009/0149766 A1 | 6/2009 | Shuros et al. |
| 2009/0177225 A1 | 7/2009 | Nunez et al. |
| 2009/0189741 A1 | 7/2009 | Rowland |
| 2009/0198293 A1 | 8/2009 | Cauller |
| 2009/0270729 A1 | 10/2009 | Corbucci |
| 2009/0299427 A1 | 12/2009 | Liu et al. |
| 2010/0056922 A1 | 3/2010 | Florent |
| 2010/0063375 A1 | 3/2010 | Kassab et al. |

(56) References Cited

U.S. PATENT DOCUMENTS

| | | |
|---|---|---|
| 2010/0076398 A1 | 3/2010 | Scheurer et al. |
| 2010/0094328 A1 | 4/2010 | O'dea et al. |
| 2010/0113939 A1 | 5/2010 | Mashimo et al. |
| 2010/0121398 A1 | 5/2010 | Bjorling et al. |
| 2010/0222786 A1 | 9/2010 | Kassab |
| 2010/0262206 A1 | 10/2010 | Zdeblick et al. |
| 2010/0324432 A1 | 12/2010 | Bjorling et al. |
| 2011/0105863 A1 | 5/2011 | Kroh |
| 2011/0144967 A1 | 6/2011 | Adirovich |
| 2011/0160844 A1 | 6/2011 | Haselby |
| 2011/0178383 A1 | 7/2011 | Kassab |
| 2011/0184301 A1 | 7/2011 | Holmstrom et al. |
| 2011/0201990 A1 | 8/2011 | Franano |
| 2011/0265908 A1 | 11/2011 | Clerc et al. |
| 2011/0306867 A1 | 12/2011 | Gopinathan et al. |
| 2012/0016207 A1 | 1/2012 | Allen |
| 2012/0029598 A1 | 2/2012 | Zhao |
| 2012/0136385 A1 | 5/2012 | Cully |
| 2012/0203090 A1 | 8/2012 | Min |
| 2012/0203113 A1 | 8/2012 | Skerl et al. |
| 2012/0291788 A1 | 11/2012 | Griswold et al. |
| 2012/0296222 A1 | 11/2012 | Griswold et al. |
| 2013/0030295 A1 | 1/2013 | Huennekens et al. |
| 2013/0041244 A1 | 2/2013 | Woias et al. |
| 2013/0041251 A1 | 2/2013 | Bailey et al. |
| 2013/0041269 A1 | 2/2013 | Stahmann et al. |
| 2013/0060139 A1 | 3/2013 | Richter |
| 2013/0073025 A1 | 3/2013 | Kassab |
| 2013/0096409 A1 | 4/2013 | Hiltner et al. |
| 2013/0178750 A1 | 7/2013 | Sheehan et al. |
| 2013/0178751 A1 | 7/2013 | Min |
| 2013/0222153 A1 | 8/2013 | Rowland et al. |
| 2013/0245469 A1 | 9/2013 | Yadav |
| 2013/0261655 A1 | 10/2013 | Drasler et al. |
| 2013/0274705 A1 | 10/2013 | Burnes et al. |
| 2013/0296721 A1 | 11/2013 | Yadav et al. |
| 2013/0303914 A1 | 11/2013 | Hiltner et al. |
| 2013/0303915 A1 | 11/2013 | Barnard et al. |
| 2013/0310820 A1 | 11/2013 | Fernandez et al. |
| 2013/0317359 A1 | 11/2013 | Wilson et al. |
| 2013/0324866 A1 | 12/2013 | Gladshtein |
| 2013/0331678 A1 | 12/2013 | Lading et al. |
| 2013/0338468 A1 | 12/2013 | Kassab |
| 2014/0028467 A1 | 1/2014 | Nagy |
| 2014/0051965 A1 | 2/2014 | Zdeblick et al. |
| 2014/0066738 A1 | 3/2014 | Kassab |
| 2014/0084943 A1 | 3/2014 | Kroh et al. |
| 2014/0088994 A1 | 3/2014 | Kroh |
| 2014/0094697 A1 | 4/2014 | Petroff et al. |
| 2014/0107768 A1 | 4/2014 | Venkatasubramanian |
| 2014/0155710 A1 | 6/2014 | Rowland |
| 2014/0155768 A1 | 6/2014 | Orion et al. |
| 2014/0155769 A1 | 6/2014 | White |
| 2014/0200428 A1 | 7/2014 | Kassab |
| 2014/0236011 A1 | 8/2014 | Fan et al. |
| 2014/0243640 A1 | 8/2014 | O'Dea |
| 2014/0266935 A1 | 9/2014 | Tankiewicz |
| 2014/0275861 A1 | 9/2014 | Kroh et al. |
| 2014/0276011 A1 | 9/2014 | Schmitt et al. |
| 2014/0276110 A1 | 9/2014 | Hoseit |
| 2014/0276121 A1 | 9/2014 | Kassab |
| 2014/0276191 A1 | 9/2014 | Kassab |
| 2014/0288085 A1 | 9/2014 | Yadav |
| 2014/0288459 A1 | 9/2014 | Yadav et al. |
| 2014/0306807 A1 | 10/2014 | Rowland |
| 2014/0330143 A1 | 11/2014 | Kroh et al. |
| 2014/0350348 A1 | 11/2014 | Tee et al. |
| 2015/0031966 A1 | 1/2015 | Ward et al. |
| 2015/0045649 A1 | 2/2015 | O'Dea et al. |
| 2015/0051467 A1 | 2/2015 | Corbucci et al. |
| 2015/0065835 A1 | 3/2015 | Kassab |
| 2015/0065897 A1 | 3/2015 | Bomzin et al. |
| 2015/0088100 A1 | 3/2015 | Oborn |
| 2015/0133796 A1 | 5/2015 | Yadav |
| 2015/0141863 A1 | 5/2015 | Kassab et al. |
| 2015/0157268 A1 | 6/2015 | Winshtein et al. |
| 2015/0208929 A1 | 7/2015 | Rowland |
| 2015/0216425 A1 | 8/2015 | Gladshtein et al. |
| 2015/0223702 A1 | 8/2015 | Vanney et al. |
| 2015/0238121 A1 | 8/2015 | Tu et al. |
| 2015/0257732 A1 | 9/2015 | Ryan |
| 2015/0282720 A1 | 10/2015 | Goldshtein et al. |
| 2015/0282875 A1 | 10/2015 | Harper et al. |
| 2015/0297110 A1 | 10/2015 | Kassab |
| 2015/0297111 A1 | 10/2015 | Kassab |
| 2015/0297112 A1 | 10/2015 | Kassab et al. |
| 2015/0297113 A1 | 10/2015 | Kassab |
| 2015/0297818 A1 | 10/2015 | Matsubara et al. |
| 2015/0305808 A1 | 10/2015 | Ku et al. |
| 2015/0313479 A1 | 11/2015 | Stigall et al. |
| 2015/0327786 A1 | 11/2015 | Lading et al. |
| 2016/0000403 A1 | 1/2016 | Vilkomerson |
| 2016/0022216 A1 | 1/2016 | Goldshtein et al. |
| 2016/0029956 A1 | 2/2016 | Rowland |
| 2016/0029995 A1 | 2/2016 | Navratil et al. |
| 2016/0081657 A1 | 3/2016 | Rice |
| 2016/0095535 A1 | 4/2016 | Hettrick et al. |
| 2016/0135787 A1 | 5/2016 | Anderson et al. |
| 2016/0135941 A1 | 5/2016 | Binmoeller et al. |
| 2016/0166232 A1 | 6/2016 | Merritt |
| 2016/0198981 A1 | 7/2016 | Demir et al. |
| 2016/0210846 A1 | 7/2016 | Rowland et al. |
| 2016/0324443 A1 | 11/2016 | Rowland et al. |
| 2016/0345930 A1 | 12/2016 | Mizukami |
| 2016/0361019 A1* | 12/2016 | Crystal ............... A61B 6/4078 |
| 2017/0055048 A1 | 2/2017 | Nagy et al. |
| 2017/0055909 A1 | 3/2017 | Schibli et al. |
| 2017/0071501 A1 | 3/2017 | Kassab |
| 2017/0065824 A1 | 8/2017 | Dagan et al. |
| 2017/0238817 A1 | 8/2017 | Lading |
| 2017/0265839 A1* | 9/2017 | Levine .................. A61B 8/445 |
| 2017/0360312 A1 | 12/2017 | Joseph |
| 2018/0064931 A1 | 3/2018 | Clements |
| 2018/0177486 A1 | 6/2018 | Gifford et al. |
| 2018/0220992 A1 | 8/2018 | Gifford et al. |
| 2018/0228951 A1 | 8/2018 | Schwammenthal et al. |
| 2018/0247095 A1 | 8/2018 | Sundaram et al. |
| 2018/0268941 A1 | 9/2018 | Lavi et al. |
| 2018/0269931 A1 | 9/2018 | Hershko et al. |
| 2018/0289488 A1 | 10/2018 | Orth et al. |
| 2018/0289536 A1 | 10/2018 | Burnett |
| 2018/0293409 A1 | 10/2018 | Sundaram et al. |
| 2019/0029639 A1 | 1/2019 | Gifford et al. |
| 2019/0046047 A1 | 2/2019 | Haase |
| 2019/0053720 A1 | 2/2019 | Sawado |
| 2019/0053767 A1 | 2/2019 | Yamada |
| 2019/0069784 A1 | 3/2019 | Mukkamala |
| 2019/0069842 A1 | 3/2019 | Rothberg |
| 2019/0069851 A1 | 3/2019 | Sharma |
| 2019/0070348 A1 | 3/2019 | Frost |
| 2019/0076033 A1 | 3/2019 | Sweeney et al. |
| 2019/0082978 A1 | 3/2019 | Van der Horst |
| 2019/0083030 A1 | 3/2019 | Thakur |
| 2019/0090760 A1 | 3/2019 | Kinast |
| 2019/0090763 A1 | 3/2019 | Woerlee |
| 2019/0090856 A1 | 3/2019 | Van der Horst |
| 2019/0099087 A1 | 4/2019 | Cros |
| 2019/0099088 A1 | 4/2019 | Whinnett |
| 2019/0110696 A1 | 4/2019 | Benkowski |
| 2019/0167188 A1 | 6/2019 | Gifford et al. |
| 2020/0013510 A1 | 1/2020 | Despenic et al. |
| 2020/0022588 A1 | 1/2020 | Wariar et al. |
| 2020/0022589 A1 | 1/2020 | Banet et al. |
| 2020/0029829 A1 | 1/2020 | Banet et al. |
| 2020/0029857 A1 | 1/2020 | Rowland et al. |
| 2020/0030612 A1 | 1/2020 | Song et al. |
| 2020/0037888 A1 | 2/2020 | Thakur et al. |
| 2020/0037892 A1 | 2/2020 | Banet et al. |
| 2020/0046299 A1 | 2/2020 | An et al. |
| 2020/0121187 A1 | 4/2020 | Sarkar et al. |
| 2020/0129087 A1 | 4/2020 | Sweeney et al. |
| 2020/0146577 A1 | 5/2020 | Badie et al. |
| 2020/0170515 A1 | 6/2020 | Wen et al. |
| 2020/0170711 A1 | 6/2020 | Hendriks et al. |

(56) References Cited

U.S. PATENT DOCUMENTS

| | | |
|---|---|---|
| 2020/0187864 A1 | 6/2020 | Sharma |
| 2020/0187865 A1 | 6/2020 | Sharma et al. |
| 2020/0196876 A1 | 6/2020 | Minor et al. |
| 2020/0196899 A1 | 6/2020 | Higgins et al. |
| 2020/0196943 A1 | 6/2020 | Minor et al. |
| 2020/0196944 A1 | 6/2020 | Minor et al. |
| 2020/0196948 A1 | 6/2020 | Cho et al. |
| 2020/0197178 A1 | 6/2020 | Vecchio |

FOREIGN PATENT DOCUMENTS

| | | |
|---|---|---|
| EP | 0538885 A1 | 4/1993 |
| EP | 0897285 A1 | 2/1999 |
| EP | 1162914 A1 | 12/2001 |
| EP | 1311210 A2 | 5/2003 |
| EP | 0904009 B1 | 9/2003 |
| EP | 1545303 A2 | 6/2005 |
| EP | 1677852 A2 | 7/2006 |
| EP | 1847217 A2 | 10/2007 |
| EP | 1851524 A2 | 11/2007 |
| EP | 1851791 A2 | 11/2007 |
| EP | 1868496 A2 | 12/2007 |
| EP | 1871224 A2 | 1/2008 |
| EP | 1893080 A2 | 3/2008 |
| EP | 1893081 A2 | 3/2008 |
| EP | 1893085 A2 | 3/2008 |
| EP | 2091426 A2 | 6/2008 |
| EP | 1948007 | 7/2008 |
| EP | 1993438 A1 | 11/2008 |
| EP | 2012658 A2 | 1/2009 |
| EP | 2046242 A2 | 4/2009 |
| EP | 2117423 A2 | 11/2009 |
| EP | 2197344 A1 | 6/2010 |
| EP | 2265164 A1 | 12/2010 |
| EP | 2021757 B1 | 4/2011 |
| EP | 2391263 A2 | 12/2011 |
| EP | 1921983 B1 | 1/2012 |
| EP | 2060014 B1 | 1/2012 |
| EP | 1902529 B1 | 6/2012 |
| EP | 1876945 B1 | 12/2012 |
| EP | 2330968 B1 | 4/2013 |
| EP | 2601633 A2 | 6/2013 |
| EP | 2449960 B1 | 10/2013 |
| EP | 2725969 A1 | 5/2014 |
| EP | 1993436 B1 | 6/2014 |
| EP | 3027109 A1 | 2/2015 |
| EP | 2076170 B1 | 4/2015 |
| EP | 2895059 A1 | 7/2015 |
| EP | 2898470 A1 | 7/2015 |
| EP | 2922465 A1 | 9/2015 |
| EP | 2317912 B1 | 11/2015 |
| EP | 1817593 B1 | 12/2015 |
| EP | 2967432 A2 | 1/2016 |
| EP | 2268218 B1 | 2/2016 |
| EP | 2456502 B1 | 4/2016 |
| EP | 2702578 B1 | 8/2016 |
| EP | 3057075 A1 | 8/2016 |
| EP | 2417590 B1 | 5/2017 |
| EP | 3359021 A1 | 8/2018 |
| EP | 3435847 A1 | 2/2019 |
| EP | 3435862 A1 | 2/2019 |
| EP | 3437000 A1 | 2/2019 |
| EP | 3448330 A1 | 3/2019 |
| EP | 3448487 A2 | 3/2019 |
| EP | 3457911 A1 | 3/2019 |
| EP | 3457924 A1 | 3/2019 |
| EP | 3457928 A1 | 3/2019 |
| EP | 3463082 A1 | 4/2019 |
| EP | 3468462 A1 | 4/2019 |
| EP | 3591663 A1 | 1/2020 |
| EP | 3609392 A1 | 2/2020 |
| EP | 3256043 B1 | 3/2020 |
| EP | 3629921 A1 | 4/2020 |
| EP | 3629937 A1 | 4/2020 |
| EP | 3630275 A1 | 4/2020 |
| EP | 3634206 A1 | 4/2020 |
| EP | 3654835 A1 | 5/2020 |
| EP | 3496808 B1 | 6/2020 |
| EP | 2654560 B1 | 7/2020 |
| EP | 3326524 B1 | 7/2020 |
| EP | 3367884 B1 | 7/2020 |
| EP | 3678539 A1 | 7/2020 |
| EP | 3681389 A1 | 7/2020 |
| EP | 3684260 A1 | 7/2020 |
| EP | 3684464 A1 | 7/2020 |
| JP | 2011234884 A | 11/2011 |
| WO | 1997042871 A1 | 11/1997 |
| WO | 1998029030 A1 | 12/1997 |
| WO | 1998035611 A1 | 8/1998 |
| WO | 2000055579 A2 | 9/2000 |
| WO | 2000056210 A1 | 9/2000 |
| WO | 2001012092 A1 | 2/2001 |
| WO | 2001013792 A1 | 3/2001 |
| WO | 2002015823 A2 | 2/2002 |
| WO | 2002076289 A2 | 10/2002 |
| WO | 2003061467 A1 | 7/2003 |
| WO | 2003061504 A1 | 7/2003 |
| WO | 2003092495 A1 | 11/2003 |
| WO | 2004014456 A2 | 2/2004 |
| WO | 2004073796 A1 | 9/2004 |
| WO | 2006049796 A2 | 5/2006 |
| WO | 2006086113 A2 | 8/2006 |
| WO | 2006086114 A2 | 8/2006 |
| WO | 2005027998 A2 | 9/2006 |
| WO | 2006094273 A2 | 9/2006 |
| WO | 2006096582 A1 | 9/2006 |
| WO | 2006102905 A1 | 10/2006 |
| WO | 2006110798 A2 | 10/2006 |
| WO | 2007002185 A2 | 1/2007 |
| WO | 2007002224 A2 | 1/2007 |
| WO | 2007002225 A2 | 1/2007 |
| WO | 2007008493 A1 | 1/2007 |
| WO | 2007028035 A2 | 3/2007 |
| WO | 2007035332 A1 | 3/2007 |
| WO | 2007047571 A2 | 4/2007 |
| WO | 2007047794 A2 | 4/2007 |
| WO | 2007061841 A2 | 5/2007 |
| WO | 2007106490 A2 | 9/2007 |
| WO | 2007106533 A2 | 9/2007 |
| WO | 2007130628 A2 | 11/2007 |
| WO | 2008031011 A1 | 3/2008 |
| WO | 2008031095 A1 | 3/2008 |
| WO | 2008051907 A1 | 5/2008 |
| WO | 2008066569 A2 | 6/2008 |
| WO | 2009006602 A1 | 1/2009 |
| WO | 2009006608 A1 | 1/2009 |
| WO | 2009006610 A1 | 1/2009 |
| WO | 2009006615 A1 | 1/2009 |
| WO | 2009025648 A1 | 2/2009 |
| WO | 2009039174 A1 | 3/2009 |
| WO | 2009111255 A1 | 9/2009 |
| WO | 2009131879 A1 | 10/2009 |
| WO | 2011060359 A2 | 11/2009 |
| WO | 2009146089 A2 | 12/2009 |
| WO | 2009146090 A1 | 12/2009 |
| WO | 2010011612 A1 | 1/2010 |
| WO | 2010088279 A2 | 8/2010 |
| WO | 2010117597 A1 | 10/2010 |
| WO | 20100117356 A1 | 10/2010 |
| WO | 2011011104 A1 | 1/2011 |
| WO | 2012015954 A1 | 2/2012 |
| WO | 2012015955 A1 | 2/2012 |
| WO | 2012019191 A2 | 2/2012 |
| WO | 2012090206 A2 | 7/2012 |
| WO | 2012140147 A3 | 10/2012 |
| WO | 2012145187 A1 | 10/2012 |
| WO | 2012149008 A2 | 11/2012 |
| WO | 2013003754 A1 | 1/2013 |
| WO | 2013142387 A1 | 9/2013 |
| WO | 2014006471 A2 | 1/2014 |
| WO | 2004014456 A2 | 2/2014 |
| WO | 2014047528 A1 | 3/2014 |
| WO | 2014054045 A1 | 4/2014 |
| WO | 2014070316 A1 | 5/2014 |

(56) References Cited

FOREIGN PATENT DOCUMENTS

| WO | 2014076620 A2 | 5/2014 |
|---|---|---|
| WO | 2014081958 A1 | 5/2014 |
| WO | 2014145531 A1 | 9/2014 |
| WO | 2014145712 A1 | 9/2014 |
| WO | 2014162181 A2 | 10/2014 |
| WO | 2014170771 A1 | 10/2014 |
| WO | 2014179739 A1 | 11/2014 |
| WO | 2014197101 A1 | 12/2014 |
| WO | 2015074018 A1 | 5/2015 |
| WO | 2015109028 A1 | 7/2015 |
| WO | 20150157712 A2 | 10/2015 |
| WO | 2016011309 A2 | 1/2016 |
| WO | 2016025430 A1 | 2/2016 |
| WO | 2016131020 A1 | 8/2016 |
| WO | 2016178196 A2 | 11/2016 |
| WO | 2016178197 A1 | 11/2016 |
| WO | 2017024051 A1 | 2/2017 |
| WO | 2017143198 A1 | 8/2017 |
| WO | 2017198867 A1 | 11/2017 |
| WO | 2017222964 A1 | 12/2017 |
| WO | 2018013725 A1 | 1/2018 |
| WO | 2018031714 A1 | 2/2018 |
| WO | 2018081314 A1 | 5/2018 |
| WO | 2018102435 A1 | 6/2018 |
| WO | 2018150314 A1 | 8/2018 |
| WO | 2018156930 A1 | 8/2018 |
| WO | 2018187582 A1 | 10/2018 |
| WO | 2018220143 A1 | 12/2018 |
| WO | 2018220146 A1 | 12/2018 |
| WO | 2019050831 A1 | 3/2019 |
| WO | 2019051007 A1 | 3/2019 |
| WO | 2019051108 A1 | 3/2019 |
| WO | 2019051007 A8 | 4/2019 |
| WO | 2019063521 A1 | 4/2019 |
| WO | 2019079364 A1 | 4/2019 |
| WO | 2020023839 A1 | 1/2020 |
| WO | 2020121221 A1 | 6/2020 |
| WO | 2020131247 A1 | 6/2020 |
| WO | 2020132460 A1 | 6/2020 |
| WO | 2020132668 A2 | 6/2020 |
| WO | 2020132669 A1 | 6/2020 |
| WO | 2020132670 A1 | 6/2020 |
| WO | 2020132671 A1 | 6/2020 |
| WO | 2020132678 A1 | 6/2020 |
| WO | 2020144075 A1 | 7/2020 |
| WO | 2020153765 A2 | 7/2020 |

OTHER PUBLICATIONS

Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.
International Search Report and Written Opinion dated Mar. 27, 2018, in connection with PCT/US2017/063749.
International Search Report and Written Opinion dated Aug. 29, 2018, in connection with PCT/EP2018/064386.
International Search Report and Written Opinion dated Aug. 21, 2018, in connection with PCT/EP2018/064383.
International Search Report and Written Opinion dated Oct. 20, 2016, in connection with PCT/US2016/045385 filed Aug. 3, 2016.
International Search Report and Written Opinion dated Feb. 27, 2020, in connection with PCT/IB2019/060669 filed Dec. 11, 2019.
Voroneanu et. al., "The relationship between chronic volume overload 3 and elevated blood pressure in hemodialysis patients: 4 use of bioimpedance provides a different perspective 5 from echocardiography and biomarker methodologies," Int Urol Nephrol, Sep. 2010; 42(3):789-97.
Cannesson et al., "Respiratory Variations in Pulse Oximetry Plethysmographic Waveform Amplitude to Predict Fluid Responsiveness in the Operating Room," Anesthesiology 2007; 106:1105-11.

Abraham et al., "The Role of Implantable Hemodynamic Monitors to Manage Heart Failure," Heart Failure Clin 11 (2015) 183-189.
Tallaj et al., "Implantable Hemodynamic Monitors," Cardiol Clin 29 (2011) 289-299.
Tang et al., "Measuring impedance in congestive heart failure: Current options and clinical applications," American Heart Journal 157 (3) 402-411.
Merchant et al., "Implantable Sensors for Heart Failure," Circulation: Arrhythmia and Electrophysiology. 2010; 3: 657-667.
Unadkat, Jignesh V., et al. "The Development of a Wireless Implantable Blood Flow Monitor," Ideas and Innovations, American Society of Plastic Surgeons, 136:199 (2015).
Steinhouse, David et al., "Implant Experience with an Implantable Hemodynamic Monitor for the Management of Symptomatic Heart Failure," PACE (Aug. 2005) vol. 28, pp. 747-753.
Braunschweig, Frieder et al. "Dynamic changes in right ventricular pressures during haemodialysis recorded with an implantable haemodynamic monitor," Nephrol Dial Transplant (2006) 21:176-183.
Karamanoglu, Mustafa et al., "Estimation of cardiac output in patients with congestive heart failure by analysis of right ventricular pressure waveforms," BioMedical Engineering OnLine 2011, 10:36.
Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.
Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.
Kjellstrom, Barbo et al., "Changes in Right Ventricular Pressures Between Hemodialysis Sessions Recorded by an Implantable Hemodynamic Monitor," The American Journal of Cardiology, 2009, 103:119-123.
Zile, Michael R. et al., "Transition From Chronic Compensated to Acute Decompensated Heart Failure," Circulation, American Heart Association (2008) 118:1433-1441.
Plicchi, G. et al., "Pea I and Pea II Based Implantable Haemodynamic Monitor: Pre Clinical Studies in Sheep," Europace (2002) 4, 49-54.
Vanderheyden, Marc et al., "Continuous Monitoring of Intrathoracic Impedance and Right Ventricular Pressures in Patients With Heart Failure," Circulation Heart Failure (2010) 3:370-377.
Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.
Muller, Laurent et al., "Respiratory variations of inferior vena cava diameter to predict fluid responsiveness in spontaneously breathing patients with acute circulatory failure: need for a cautious use," Critical Care 2012, 16:R188.
Blehar, David J. et al., "Identification of congestive heart failure via respiratory variation of inferior vena cava diameter." American Journal of Emergency Medicine (2009) 27, 71-75.
Miller, Joseph B., et al., "Inferior vena cava assessment in the bedside diagnosis of acute heart failure," American Journal of Emergency Medicine (2012) 30, 778-783.
Corl, Keith et al., "Bedside sonographic measurement of the inferior vena caval index is a poor predictor of fluid responsiveness in emergency department patients," Emergency Medicine Australasia (2012) 24, 534-539.
Feissel, et al. "The respiratory variation in inferior vena cava diameter as a guide to fluid therapy," Intensive Care Med (2004) 30: 1834-1837.
Nakao, Shoichiro et al., "Effects of Positional Changes on Inferior Vena Caval Size and Dynamics and Correlations with Right-Sided Cardiac Pressure," American Journal of Cardiology (1987; 59:125-132).
Saha, Narayan M., et al., "Outpatient Use of Focused Cardiac Ultrasound to Assess the Inferior Vena Cava in Patients With Heart Failure," American Journal of Cardiology (2015).
Ishizaki, et al. "Measurement of inferior vena cava diameter for evaluation of venous return in subjects on day 10 of a bed-rest experiment," J Appl Physical 96: 2179-2186, 2004.

(56) References Cited

OTHER PUBLICATIONS

Carbone et al. "Inferior Vena Cava Parameters Predict Re-admission in Ischaemic Heart Failure", European Journal of Clinical Investigations, 2014, 44(4): 341-349.
Bertram, C.D. et al., "Cross-sectional area measurement in collapsed tubes using the transformer principle", Med. & Biol, Eng. & Comput, 1989, 27, 357-364.
Moreno, Augusto et al., "Mechanics of Distension of Dog Veins and Other Very Thin-Walled Tubular Structures", Circulation Research, vol. XXVII, Dec. 1970, pp. 1069-1080.
Tafur, Emilio et al., "Simultaneous Pressure, Flow and Diameter of the Vena Cava with Fright and Exercise", Circulation Research, vol. XIX, Jul. 1966., pp. 42-50.
Guntheroth, Warren G., et al., "Effect of Respiration on Venous Return and Stroke Volume in Cardiac Tamponade", Circulation Research, vol. XX, Apr. 1967, pp. 381-390.
Bartels, Lambertus et al., "Improved Lumen Visualization in Metallic Vascular Implants by Reducing RF Artifacts", Magnetic Resonance in Medicine 47:171-180 (2002).
Guntheroth, Warren G., "in Vivo Measurement of Dimensions of Veins with Implications Regarding Control of Venous Return", IEEE Transactions on Bio-Medical Engineering, Oct. 1969; pp. 247-253.
Kivelitz, Dietmar et al., "A Vascular Stent as an Active Component for Locally Enhanced Magnetic Resonance Imaging", Investigative Radiology, vol. 38, No. 3, 147-152 (2003).
Reddy, Reddy R.V., et al., "A Catheter-Tip Probe for Dynamic Cross-Section Area Measurement", pp. 149-158. (1973).
Stegall, H. Fred, "Survey of Dimension Transducers", Chronically Implanted Cardiovascular Instrumentation, pp. 107-115 (1973).
D. H. Berge!, "The Measurement of Lengths and Dimensions", Cardiovascular Fluid Dynamics, vol. 1. pp. 91-114 (1972).
Baan, Jan et al., "Dynamic Local Distensibility of Living Arteries and its relation to Wave Transmission", Biophysical Journal, vol. 14, (1974); pp. 343-362.
International Search Report and Written Opinion in connection with PCT/US2016/017902, dated Jul. 27, 2016.
Reems, Miryam et al., Central Venous Pressure: Principles, Measurement, and Interpretation, Vetlearn.com, Jan. 2012, Compendium: Continuing Education for Veterinarians, pp. E1-E10.
Yamauchi, Hideko et al., "Correlation Between Blood Volume and Pulmonary Artery Catheter Measurements", Department of Surgery and Surgical Critical Care, University of Hawaii, 2005.
Abraham, William T. et al., "Wireless pulmonary artery haemodynamic monitoring in chronic heart failure: a randomised controlled trial"; www.thelancet.com, vol. 377, Feb. 19, 2011, pp. 658-666.
Guiotto, Giovanna et al., "Inferior vena cava collapsibility to guide fluid removal in slow continuous ultrafiltration: a pilot study", Intensive Care Med (2010) 36:696-696.
Martens, Pieter et al., "Current Approach to Decongestive Therapy in Acute Heart Failure", Curr Heart Fail Rep (2015) 12:367-378.
Dupont, Matthias et a., "Impact of Systemic Venous Congestion in Heart Failure", Curr Heart Fail Rep (2011) 8:233-241.
Marik, Paul E. et al., "Hemodynamic parameters to guide fluid therapy", Annals of Intensive Care 2011, 1:1; http://www.annalsofintensivecare.com/content/1/1/1.
Silverberg, Donald et al., "The association between congestive heart failure and chronic renal disease", Curr Opin Nephrol Hypertens 13: 163-170, 2004.
International Search Report and Written Opinion dated Nov. 4, 2019, in connection with PCT/US2019/034657, filed on May 30, 2019.
Extended European Search Report dated Jul. 3, 2020, in connection with EP20163433.4.
International Search Report and Written Opinion dated Mar. 3, 2020, in connection with PCT/US2019/066589 filed Dec. 16, 2019.

* cited by examiner

DEVICES AND METHODS FOR MEASUREMENT OF VENA CAVA DIMENSIONS, PRESSURE AND OXYGEN SATURATION

FIELD OF THE INVENTION

The present invention generally relates to the field of catheter-based medical diagnostic devices and systems, including those integrated with therapeutic devices. In particular, the present invention is directed to devices and methods for measurement of vena cava dimensions, pressure, and oxygen saturation for monitoring and treating heart failure related conditions.

BACKGROUND

Central Venous Pressure (CVP) catheters have been in use for decades to track patients' venous pressures. CVP may provide an indication of cardiac preload and help determine whether changes in fluid will improve cardiac output. However, while CVP monitoring is a useful tool in managing fluid volume, increasing evidence suggests that CVP is not in itself an accurate indicator of preload or volume responsiveness. Further, the relationship of CVP to blood volume/ intravascular volume or total body fluid volume is limited at best.

It has been recognized that the diameter, area, shape and/or volume (hereafter referred to as volume) of the Inferior Vena Cava (IVC) or variation in the diameter, area, shape and/or volume of the IVC that occurs with breathing may correlate well with a patient's blood volume, and that monitoring changes in IVC volume could be a useful way to guide hemodynamic therapy. However, devices have not been developed that would enable continuous monitoring of IVC volume over extended periods of hospitalization. Further, the measurement of IVC volume along with other important parameters such as CVP and venous oxygen saturation could together provide a much more accurate picture of the patient's volume status to guide therapy. But the continuous measurement of these parameters with separate intravascular devices in the central venous system (the Vena Cavae) is not clinically practical.

SUMMARY OF EMBODIMENTS

Embodiments of the present disclosure address acute (typically about 1-30 days) management of patients whose parameters of fluid volume, pressure, and/or venous oxygen saturation of the IVC are of interest. This can include patients in fluid overload, patients who are hypovolemic, patients in shock, patients at risk of shock, patients with active bleeding, pneumonia, ARDS, cardiogenic shock, sepsis, systemic inflammatory response syndrome (SIRS), pulmonary edema, COPD, acute kidney injury (AKI), acidosis, alkalosis, dialysis patients, preoperative, intraoperative, or postoperative cardiac surgery patients, or any other heart failure or non-heart failure patients in whom circulating fluid volume, pressure, and/or oxygen saturation can be a useful measure.

In one implementation, the present disclosure is directed to a catheter for monitoring a vascular lumen dimension. The catheter includes an elongate catheter body having proximal and distal ends, the distal end configured for placement within a patient's vasculature, a distal end region configured and dimensioned to engage a wall of the vascular lumen to maintain the position of the distal end region with respect to the vascular lumen wall, and at least one detection element configured to detect lumen diameter at a monitoring location disposed in the distal end region of the catheter body. In an exemplary embodiment, the detection element includes an ultrasound transducer. The catheter body and distal end region may be configured for placement in the inferior vena cava (IVC) with an anchor element disposed in the distal end region configured to securely position the ultrasound transducer with respect to the IVC wall. The anchor element may be disposed at a longitudinal distance from the ultrasound transducer sufficient to isolate the ultrasound transducer from distortions of the vessel caused by the anchoring element. In a further exemplary embodiment, an anchor isolation structure is positioned between the ultrasound transducer and the anchor element, the anchor isolation structure including a member having sufficient stiffness to maintain the ultrasound transducer substantially in contact with the IVC wall with the ultrasound transducer oriented substantially in the direction of the IVC wall opposite the transducer.

In another implementation, the present disclosure is directed to a catheter-based monitoring system, including the catheter embodiment as described herein, including the first and second detection elements as echo-reflective elements. Such a system may further include an external device adapted to communicate with the first and second detection elements and to generate a signal correlated to the distance between the first and second detection elements.

In yet another implementation, the present disclosure is directed to a diagnostic and therapeutic system for treating a patient. This system includes an embodiment of a catheter-based diagnostic device as described herein, as well as at least one control module is configured to receive a signal indicative of the lumen diameter from the catheter-based diagnostic device and generate therapy control instructions based on the signal and a predetermined control algorithm. The system may further include a therapeutic device configured to receive the therapy control instructions from the control module and deliver therapy to the patient based upon instructions.

In still another implementation, the present disclosure is directed to a method of monitoring a dimension of a vascular lumen. The method includes inserting a catheter into the vasculature of a patient, the catheter including at least one detection element in a distal end region of the catheter, positioning a distal end region of the catheter with at least one detection element at a monitoring location in the vascular lumen, engaging the wall of the vascular lumen with the catheter to maintain at least one detection element at the monitoring location without distorting the lumen shape at the monitoring location, generating a signal with at least one detection element indicative of lumen diameter at the monitoring location, and determining a lumen dimension based on the signal.

BRIEF DESCRIPTION OF THE DRAWINGS

For the purpose of illustrating the disclosed embodiments, the drawings show aspects thereof. However, it should be understood that the disclosed embodiments are not limited to the precise arrangements and instrumentalities shown in the drawings, wherein.

DETAILED DESCRIPTION

Figure 1:
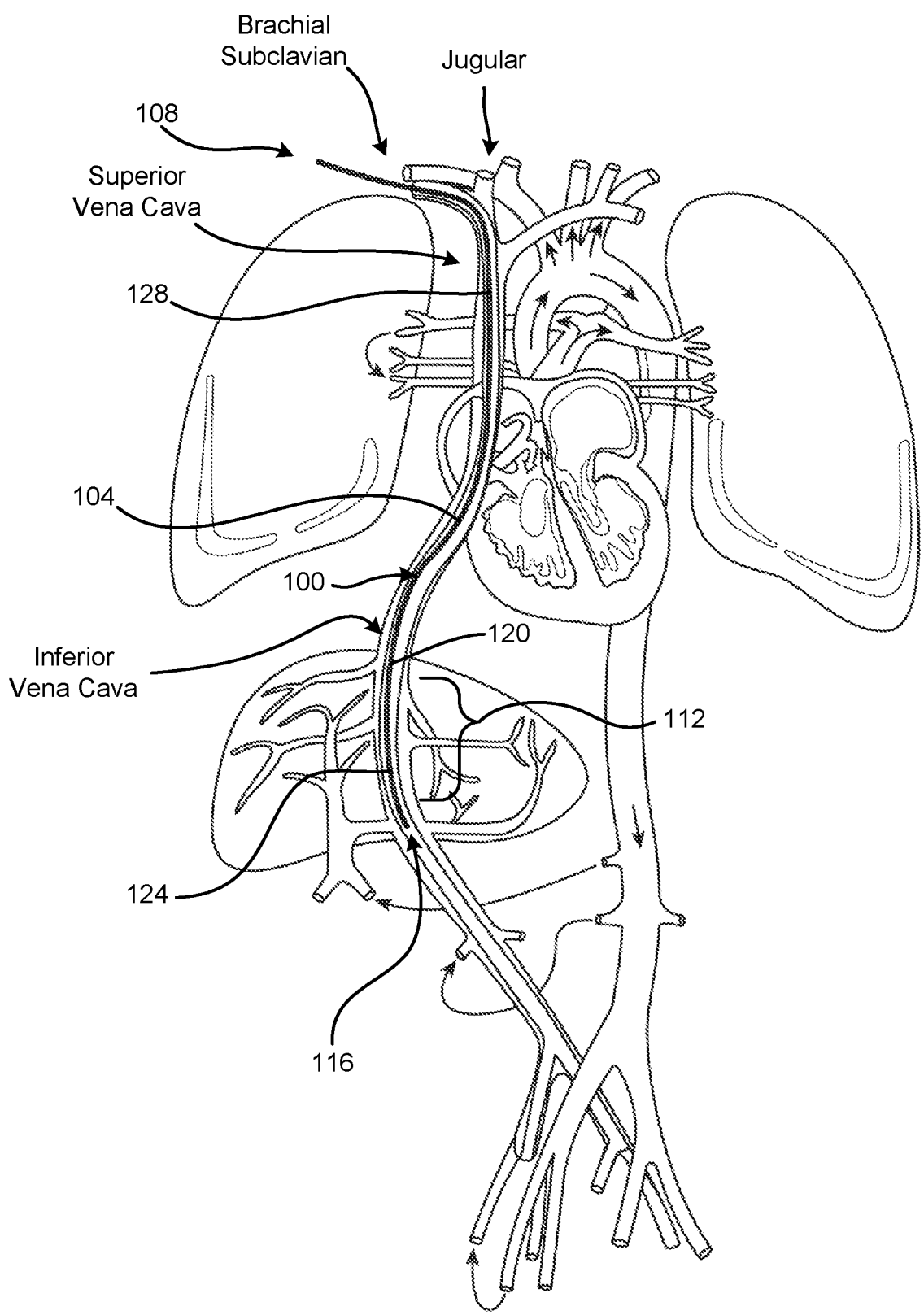
FIG. 1 schematically illustrates placement of an embodiment disclosed herein in the vascular system of a patient.

Embodiments of the present disclosure are directed to devices, systems and methods including a catheter placed in the patient's venous system that measures the volume of the Inferior Vena Cava (IVC), Superior Vena Cava (SVC), or other great vessel or branch thereof. "Vena Cava" as generally used herein, unless otherwise specified, may refer to portions of both the IVC and SVC where devices of disclosed embodiments may be placed and may sense. In some preferred embodiments, devices include an indwelling catheter that can be left in place during a patient's hospitalization in order to continuously monitor venous volume over an extended period. In other preferred embodiments, catheters according to the present disclosure measure cross-sectional size or diameter of the vessel as a proxy for vessel volume employing active or passive detection elements as described. In general, passive detection elements are elements that react in a detectable manner to a signal directed at them, such as by reflection or inducing of current flow. Passive detections elements generally do not create their own signal, whereas active detection elements generate or emit a signal that is modulated in a detectable manner based on distances it encounters. Examples of active detection elements include ultrasound transducers, light emitters and electrodes.

In some embodiments, the disclosed catheters are capable of measuring the anterior-posterior diameter of the IVC, in the area caudal to the right atrium and cranial to the renal veins. In addition to measuring this absolute diameter dimension, the catheters may also measure the variation of this diameter over the respiratory cycle, or between different modes of breathing. In another embodiment, the catheters measure the anterior-posterior diameter of the SVC, and measure variation of this diameter over the respiratory cycle, or between different modes of breathing. In some embodiments these volume measurements would be taken in both the SVC and IVC, and in other embodiments only in either the SVC or IVC. Catheters according to the invention may also measure the cross-sectional dimensions of other venous and arterial vessels, cardiovascular and other organs, structures of the digestive, renal, pulmonary, or reproductive systems, and abnormal physiologies such as aneurysms.

In other embodiments, the disclosed catheters measure venous pressure in addition to measuring venous vessel volume. In other embodiments the catheters measure central venous oxygen saturation in addition to vessel volume and pressure. In such embodiments, the catheter can provide central venous pressure data, venous volume data, and venous oxygen saturation data. The measurements of pressure, volume, and venous oxygen saturation provide clearer guidance in understanding clinical diagnosis and management in the acute setting, when timing and choice of therapy is crucial. Central venous oxygen saturation provides a surrogate measure of oxygen flux, reflecting the balance between oxygen delivery (DO2) and consumption (VO2). In certain embodiments, central venous oxygen saturation may be measured in the SVC, IVC, or both.

In further embodiments, disclosed catheters are capable of measuring oxygen saturation at multiple locations along the catheter, such as proximally in the SVC and distally in the IVC, along with pressure and/or volume at one or more points along the catheter in the great vessel (Vena Cava). Traditionally venous oxygen saturation has been measured in the pulmonary artery. However, catheterization of the pulmonary artery is costly and creates additional risks for the patient.

In further embodiments, disclosed catheters measure the change in venous oxygen between the IVC and SVC without needing to place a device in the heart. In healthy individuals, the kidneys receive a high proportion of cardiac output, but do not consume much oxygen, thus the blood in the IVC has higher oxygen content than that in the SVC. However, in situations of decreased oxygen delivery, such as heart failure, hypovolemia, or hemodynamic instability, blood flow to the brain and heart are increased, and blood flow to abdominal organs is decreased. In these acute situations, the venous oxygen saturation in the IVC may be less than in the SVC, indicating acute (severe) decompensation. The difference in IVC and SVC oxygen saturation (whether measured intermittently or trended continuously) may therefore provide a useful measurement in cardiac parameters regarding perfusion to organs in critically-ill patients. By measuring this change in IVC and SVC venous oxygen saturation, along with measuring changes of volume and pressure in the vena cava, the devices in this disclosure provide a novel diagnostic tool for managing patients in the acute setting.

Catheters as disclosed herein, such as catheter 100 of FIG. 1, which may include a body 104, a proximal end 108, a distal end region 112, and a distal end 116, may be placed into the bloodstream via a percutaneous puncture into the subclavian, brachial, or jugular vein. In such an embodiment, the disclosed catheter would then be gently advanced into the IVC, preferably over a flexible guidewire to reduce the risk of vascular trauma or puncture. In order to facilitate placement of this catheter at the bedside in the hospital ward or ICU, it may be preferable to be able to place the catheter without fluoroscopic guidance.

In one exemplary embodiment, as shown in FIG. 1, catheter 100 may include a distal region pressure sensor port 120 and a distal region oxygen saturation sensor port 124, as well as a proximal oxygen saturation sensor port 128. As discussed above, oxygen saturation sensor ports 124, 128 may be positioned on catheter 100 so as to be located, respectively, in the IVC and SVC when the catheter is properly placed in the vasculature. In another alternative, a lumen of the catheter could be used to monitor the vascular pressure at distal end 116 of catheter 100, so that if the catheter were inadvertently advanced into the right ventricle instead of the IVC, the right ventricular pressure would be detected, and the catheter could be retracted, turned, and advanced into the IVC.

Once advanced into the IVC, catheter 100 may need to be specifically oriented in one direction in the IVC, and it may be important to determine how cranial or caudal the sensor is with respect to specific anatomical markers. To do this, in some embodiments, an element of disclosed systems is an external sensor or reflector (not shown) which can be placed on the patient's abdomen during placement. If a reflector is used, catheter 100 can be rotated and advanced or retracted (or the reflector moved around on the patient's abdomen) until a strong signal is reflected to the catheter. Catheter 100 and reflector can then be moved or manipulated until the catheter is in an appropriate location and orientation.

Figure 14:
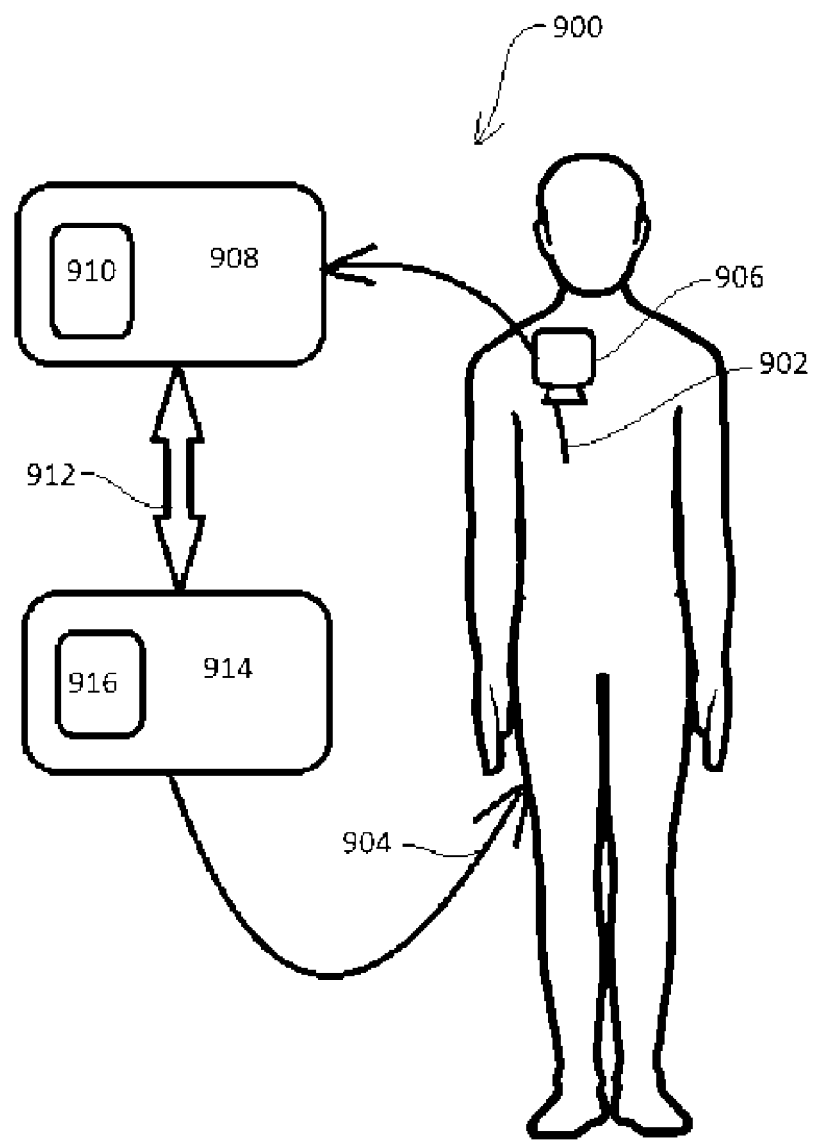
FIG. 14 is a schematic illustration of an exemplary system according to the present disclosure.

An external ultrasound system (see, e.g., FIG. 14) may also be used to confirm placement of a central venous pressure and volume (CVPV) (or central venous pressure, volume and oxygen (CVPVO)) catheter at the correct location in the IVC with correct orientation. Markers on a distal portion on the CVPV (or CVPVO) catheter that are detectable by ultrasound can be used to guide correct orientation and placement of distal sensors in the IVC.

Figure 2:
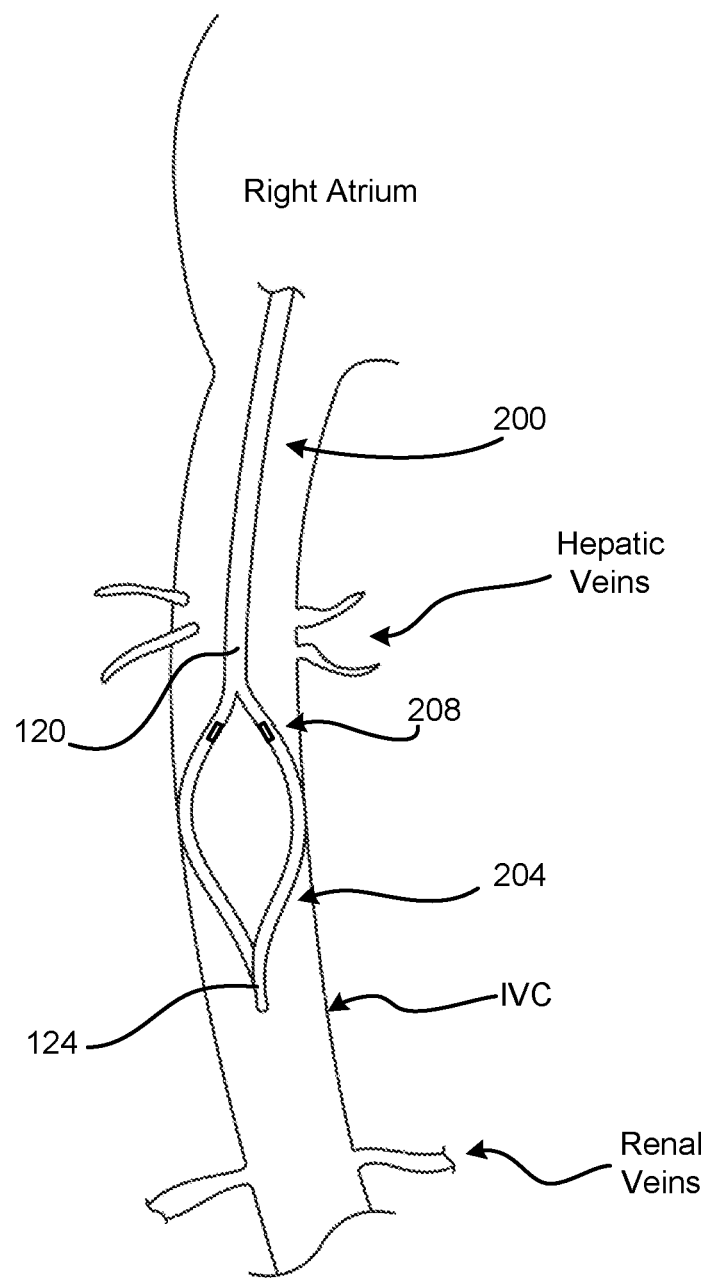
FIG. 2 is a sketch of the distal portion of a catheter with distal arms for sensing IVC diameter according to one embodiment disclosed herein.
Figure 3:
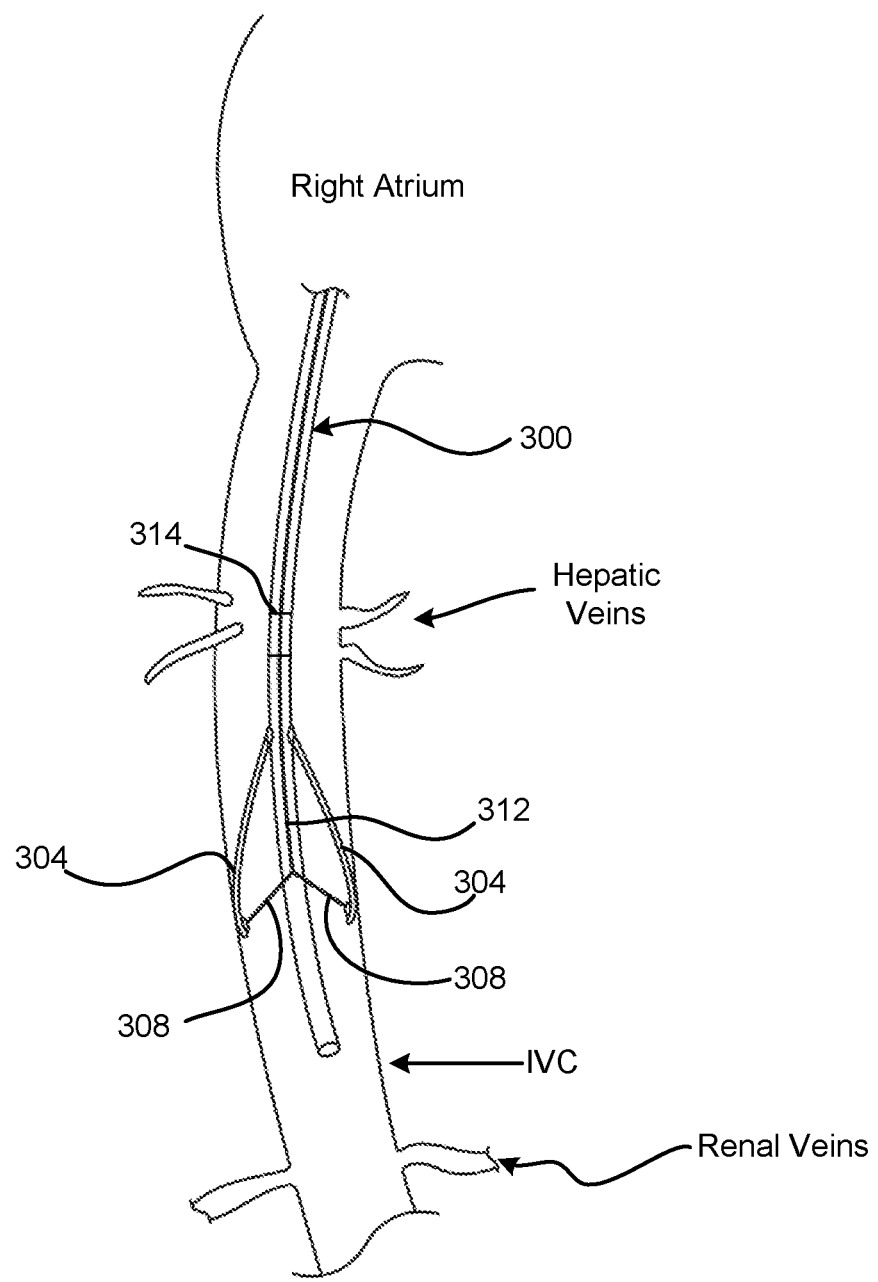
FIG. 3 is a sketch of the distal portion of another catheter with distal arms for sensing IVC diameter according to an alternative embodiment disclosed herein.

In systems and methods disclosed herein there can be several approaches to sensing IVC diameter once a catheter like catheter 100 has been delivered to the appropriate location in the IVC. One such embodiment involves mechanical measurement of the IVC, in which, for example, a catheter like catheter 200 or 300 may be provided with two or more arms 204, 304, as shown in FIGS. 2 and 3, respectively. Arms 204, 304 may be biased radially outwards to lay gently against the IVC walls. This bias may be continuous, or the arms may be held in a collapsed position until a reading is to be taken and then deployed to engage the IVC walls to take the reading. In preferred embodiments, this bias will be very gentle, since the pressure in the IVC is typically 5-20 mm HG and any strong pressure will tent the IVC open. The separation of arms 204, 304 could be measured in various ways, such as by using one or more strain gauges, such as strain gauges 208 shown in FIG. 2, on one or more arms that electronically sense flexure and transmit readings to a processor outside the body (not shown). Alternatively, a catheter like catheter 300 of FIG. 3 may include one or more linkages like linkages 308 designed and configured to convert radial expansion of the arms to longitudinal motion of a wire 312 extending through the catheter that can be monitored electronically by a detector 314, which may be located within the distal end as shown or, alternatively, at the proximal end of the catheter.

Figure 4:
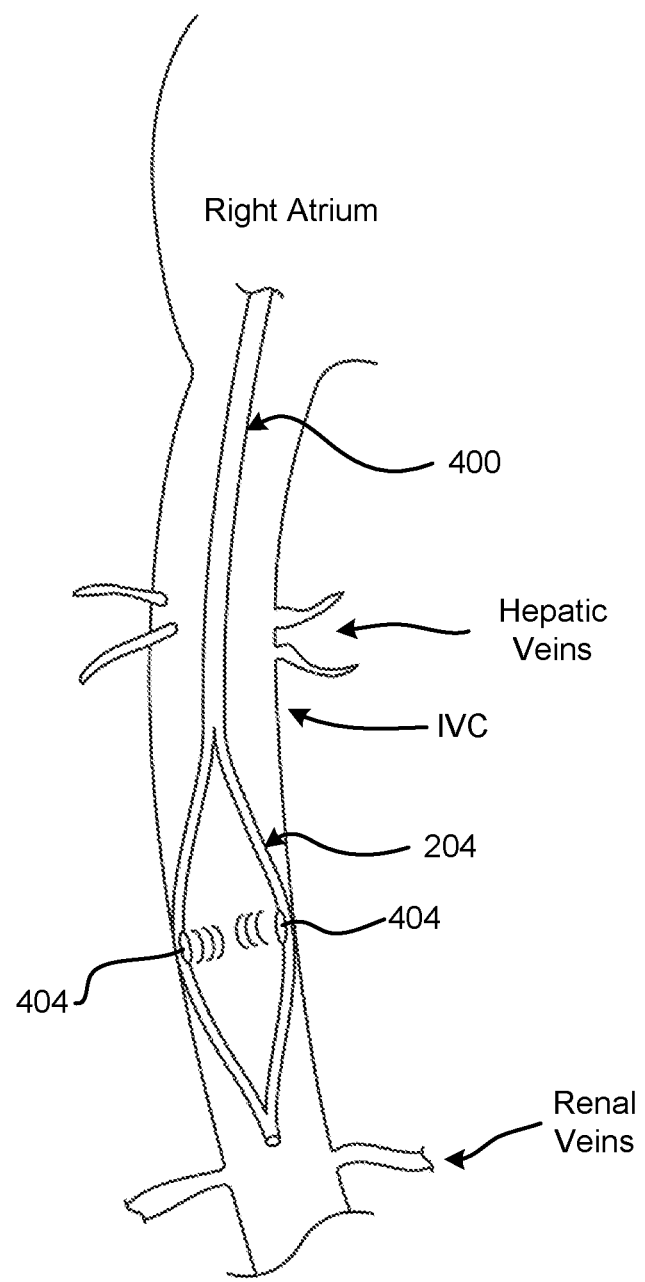
FIG. 4 is a sketch of the distal portion of a catheter with distal arms including ultrasound devices for sensing IVC diameter according to a further alternative embodiment disclosed herein.

Electronic emitters and detectors may also be mounted to each arm to electronically sense the distance between them. FIG. 4 shows a catheter 400 with two arms 204 with simple ultrasound transducers 404 on each arm. In some embodiments, more or fewer than two arms and more or fewer than one transducer per arm may be used. A signal generated by transducer 404 can be sensed by another transducer, and a simple time-of-travel calculation would determine the distance between the arms. A signal may be generated by each transducer 404 in sequence and sensed by each of the others, thereby generating a very reliable map of the relative position of each arm. Alternatively, as shown in FIG. 4A, two or more electronic emitter/detectors 408, or two or more separate emitters and detectors, may sense the electrical impedance or capacitance, at one or more frequencies, by inducing or otherwise generating and monitoring an electrical current in order to determine the volume of blood between emitter/detectors 408 or separate emitters and detectors.

It should be noted that various arm configurations are possible in each of these embodiments. A pair of arms 304, 412 may have a wishbone shape as shown in FIGS. 3 and 4A, respectively, rather than being joined at their ends as with arms 204 of FIGS. 2 and 4. These designs may be optimized to minimize rotational or longitudinal migration once the catheter has been positioned. For this purpose the arms may have a blade like shape, or flow directing fin elements added) to minimize flow resistance or to create a response to the flow, such as to provide flow-induced biasing of the arms against the vessel wall. In a further alternative, a lumen of the catheter may be used to apply suction to ports on the arms to facilitate engagement with the IVC wall.

Catheters in embodiments of systems disclosed herein may also include more than two arms, e.g., two pairs of arms arranged orthogonally to each other so as to measure the vessel in two dimensions. In still further embodiments, disclosed catheters may include a larger plurality of arms, e.g., six or more, distributed around the circumference of the catheter and configured to extend radially like spokes of a wheel when deployed. Such a configuration may eliminate the need to position the catheter rotationally within the vessel. The arms may also comprise, as shown in FIG. 4B, a circumferential array of very thin wires or fibers 416 to create a brush-like structure so as to minimize deformation of the vessel. In one embodiment, each wire/fiber 416 in such an array may comprise an optical fiber through which light may be emitted by emitters 420 and detected by an optical detector 424 on the catheter. Distance may be determined, for example, in accordance with the magnitude of light intensity received by detector 424. Alternatively, an ultrasonic reflector may be placed at the tip of each wire 416 in such an array in place of emitters 420, with an ultrasound transducer located on the catheter centrally within the array in place of detector 424 to emit and detect an ultrasound signal reflected from the reflector on the tip of each wire. Alternatively, each wire 416 may have an ultrasound detector, measuring the time of travel of an ultrasound signal from one or more ultrasound emitters. Such an embodiment may be configured to provide a two-dimensional profile of the size and shape of the vessel around its entire circumference.

Figure 4A:
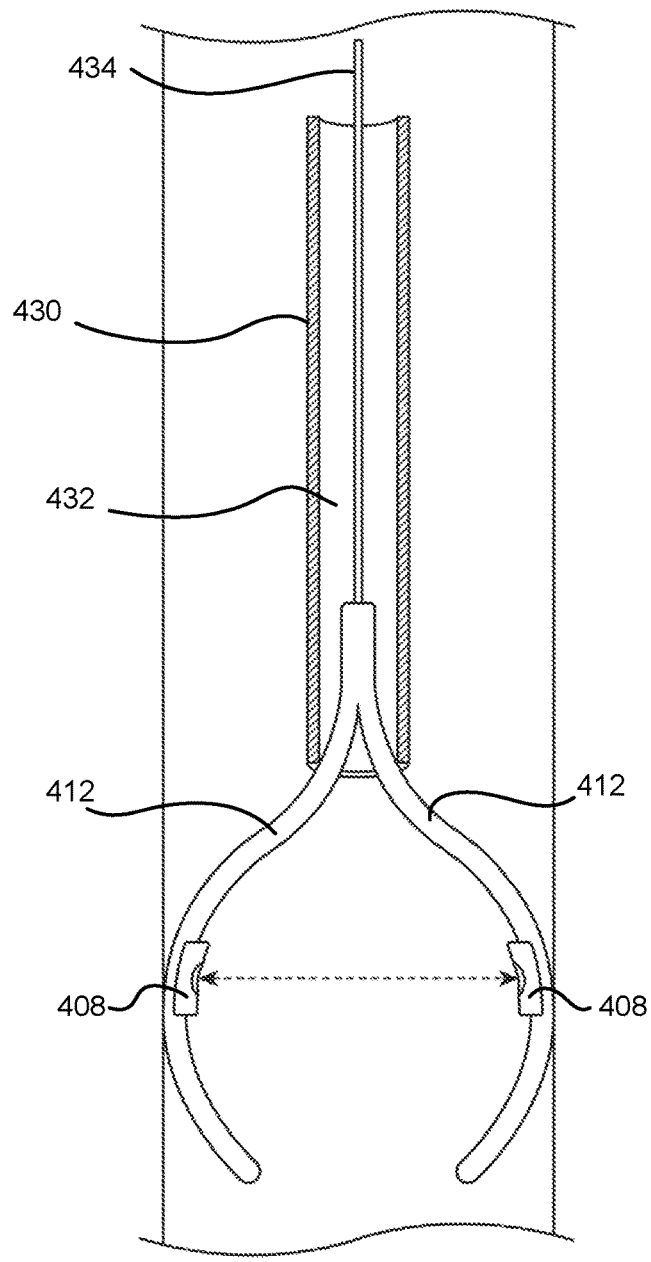
FIG. 4A is a sketch of the distal portion of a catheter with separate distal sensing arms according to a further alternative embodiment disclosed herein.
Figure 4B:
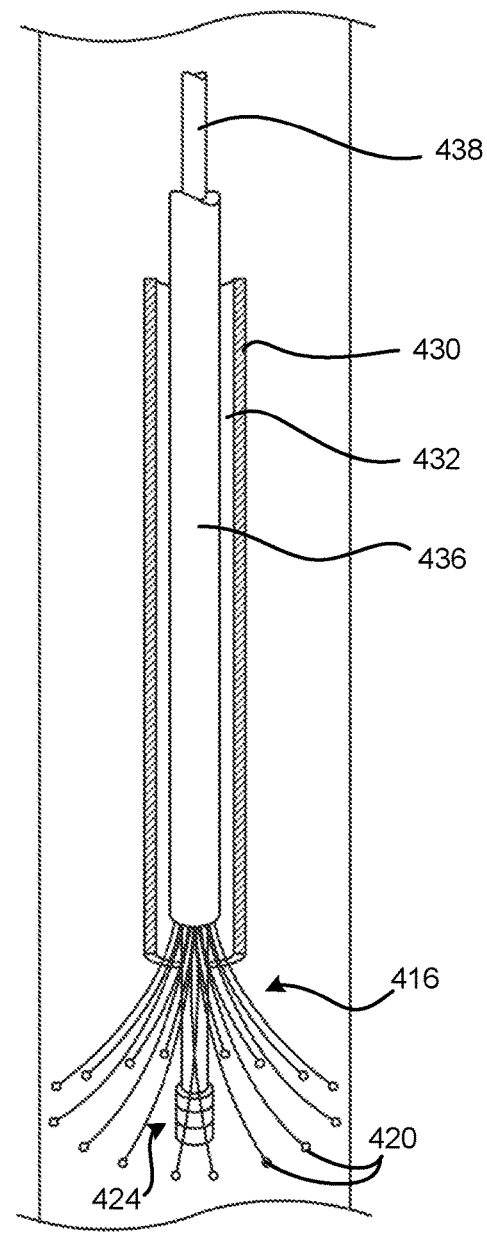
FIG. 4B is a sketch of the distal portion of a catheter with a plurality of distal sensing arms according to a further alternative embodiment disclosed herein.

FIGS. 4A and 4B also illustrate other features of the present disclosure, which may be utilized in combination with other embodiments disclosed herein as well as the embodiments of FIGS. 4A and 4B. For example, each embodiment comprises a concentric, multi-component catheter structure. In FIG. 4A, outer sheath 430 defines lumen 432, which serves as a guide catheter for inner flexible member 434, which delivers arms 412. Lumen 432 also may be used as a delivery or sampling lumen. The embodiment of FIG. 4B includes at least three concentric members, outer sheath 430, inner delivery catheter member 436, which itself defines a lumen for delivering detector carrying member 438.

Figure 5:
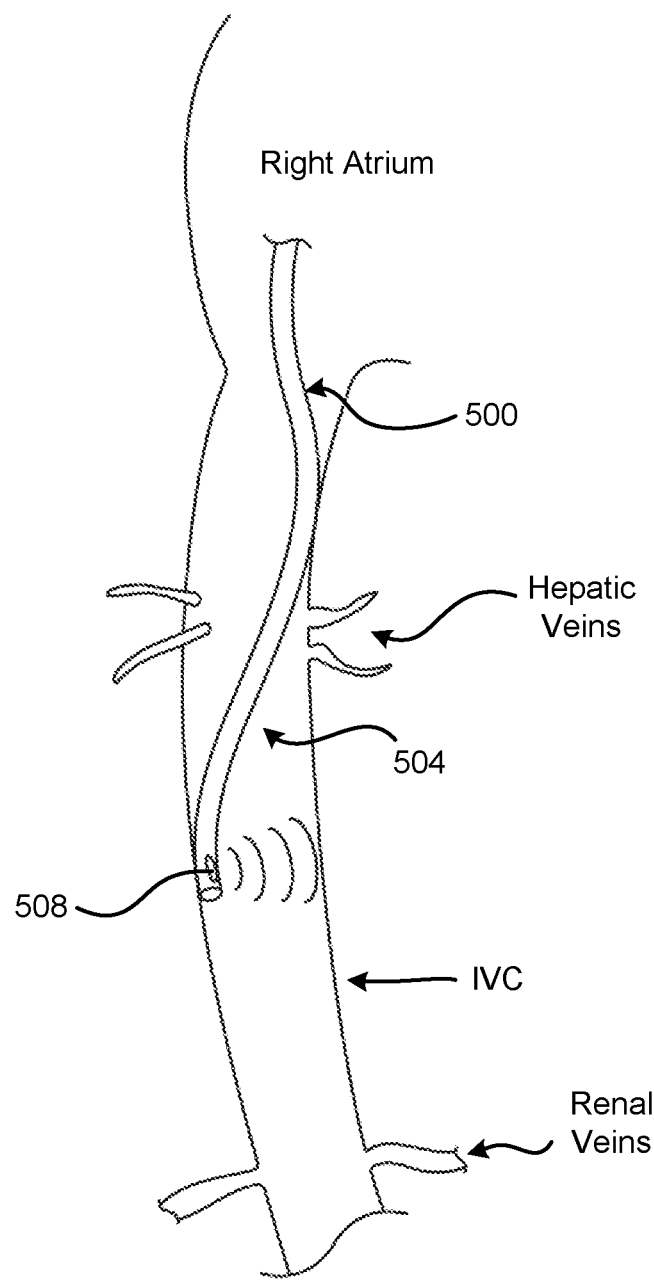
FIG. 5 is a sketch of the distal portion of an embodiment of a catheter employing ultrasound signals to measure IVC diameter in which the catheter shaft is configured with a bias to position it against a wall of the IVC.
Figure 6:
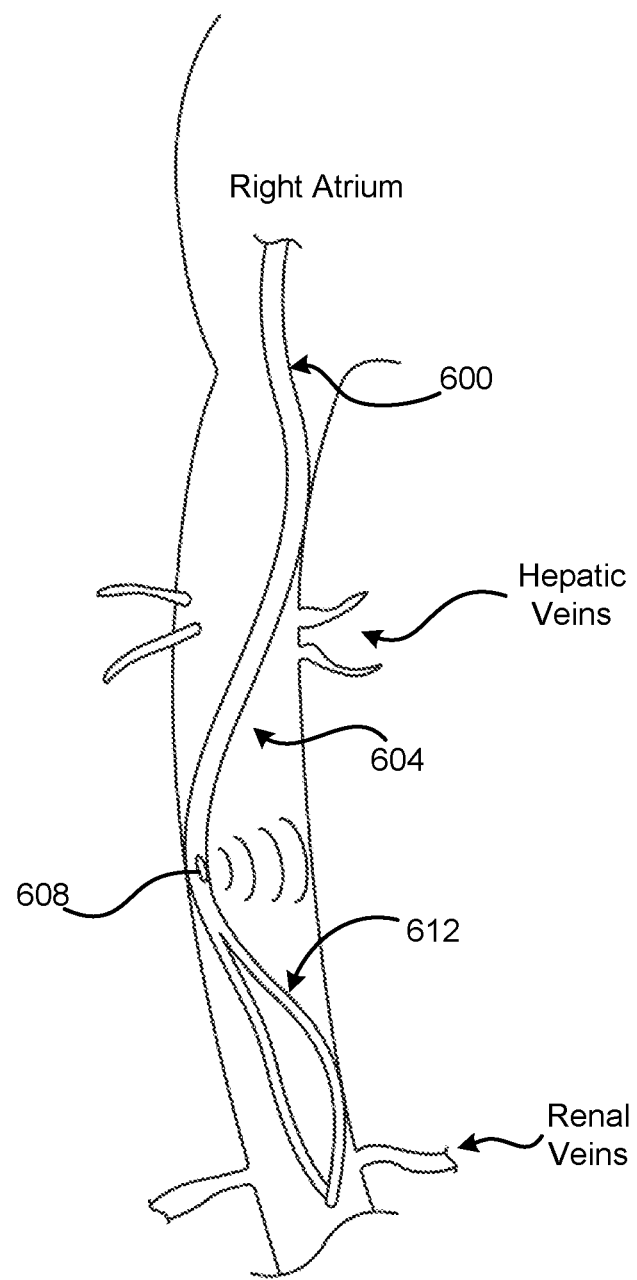
FIG. 6 is a sketch of the distal portion of another embodiment of a catheter employing ultrasound signals to measure IVC diameter in which the catheter shaft is also configured with a bias as in the embodiment of FIG. 5, but also includes a further distal portion with separable arms.
Figure 7:
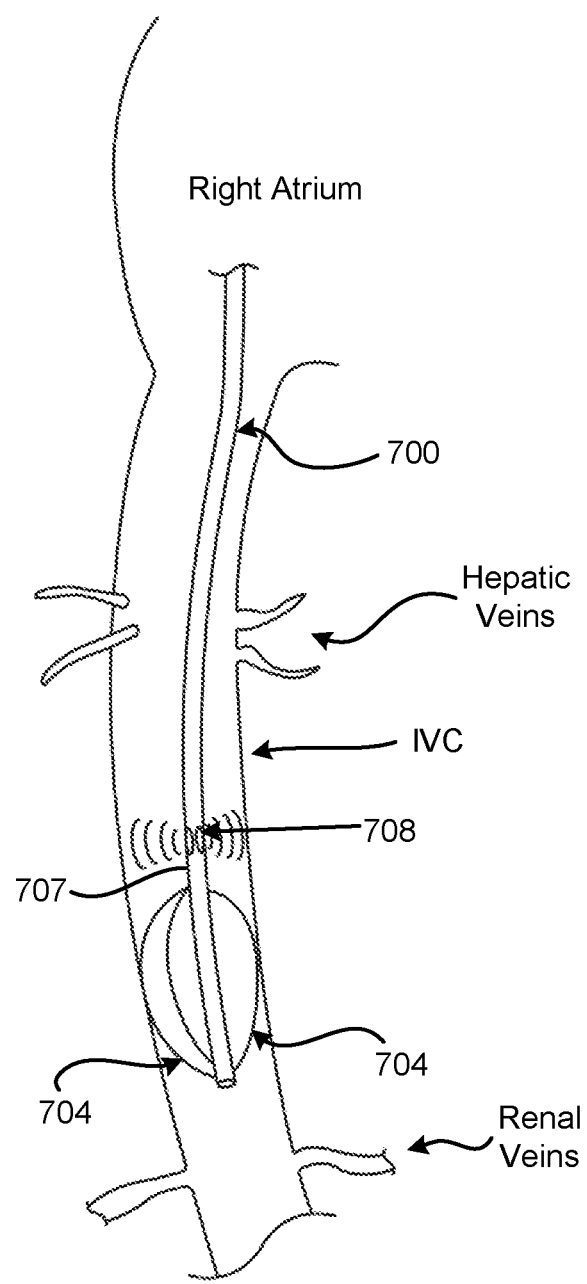
FIG. 7 is a sketch of the distal portion of a further embodiment of a catheter employing ultrasound signals to measure IVC diameter employing a plurality of elements at the distal end position of the ultrasound element centrally within the IVC.
Figure 8:
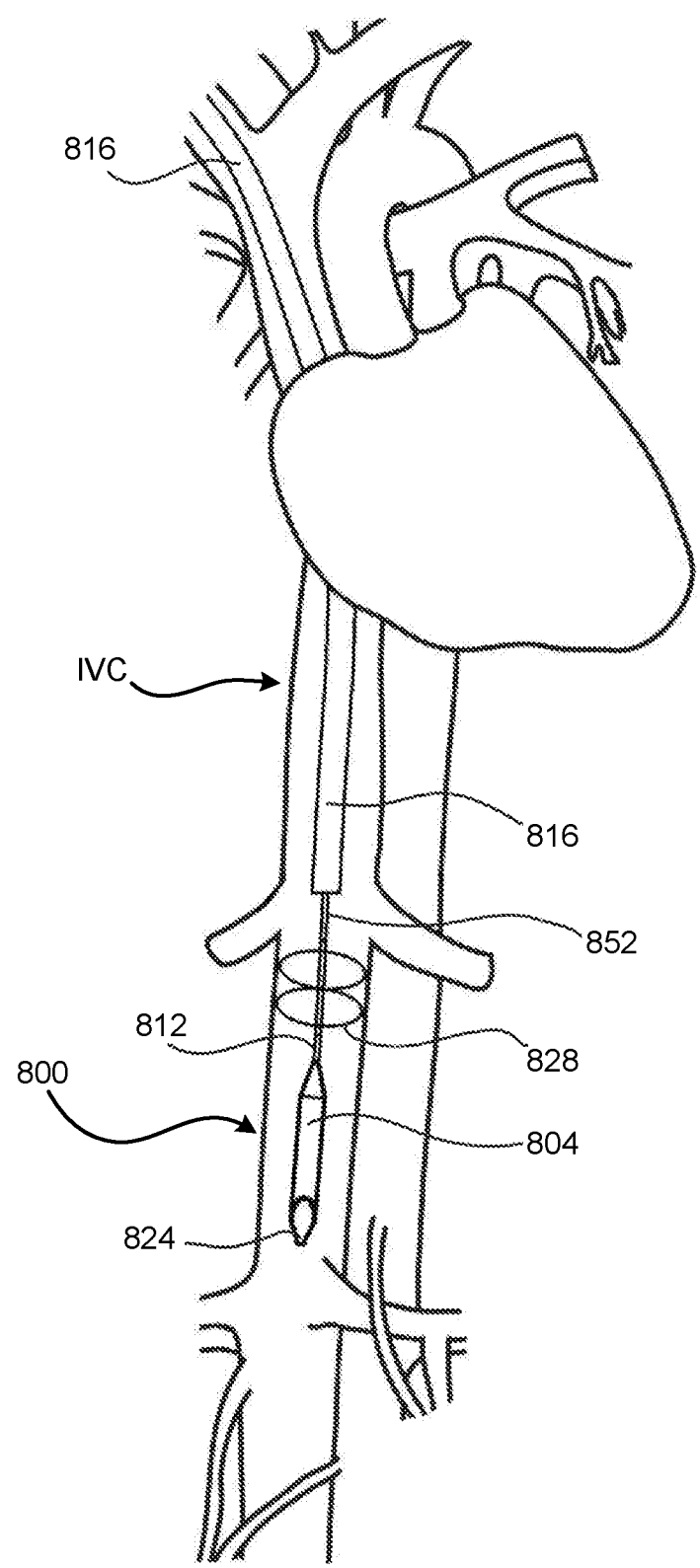
FIG. 8 is a diagram of a device made in accordance with aspects of the present invention that is disposed within the IVC via a catheter inserted through the superior vena cava.

FIGS. 5, 6, and 7 show alternative designs for embodiments of methods and systems employing catheters using ultrasound signals to measure IVC diameters. In FIGS. 5 and 6, catheters 500 and 600 have a built-in bias or curve 504, 604, which holds it against the wall of the IVC. This curve could be created by inserting a pre-shaped wire into a lumen within the catheter, either permanently or after it has been placed into the IVC. This curve might be helpful during catheter insertion, to make it easier to steer the catheter into the IVC instead of the right ventricle. Alternatively the catheter may comprise a polymeric shaft which is heat set into the desired shape. For delivery, the catheter can be inserted into a sheath or designed with a lumen to receive a stylet which straightens the shaped portion of the catheter.

In one embodiment, as shown in FIG. 5, one or more ultrasound transducers, such as ultrasound transducer 508 located at the distal end of catheter 500, may emit signals and measure the reflected signal. The wall of the IVC is relatively much more echo-reflective than the blood within the IVC, so that this reflected signal can be detected. An analysis of the distance measurements from the reflected signal(s) can then be used to determine the diameter of the IVC. While curve 504 shown in FIG. 5 may be helpful, in some embodiments the catheter alternatively may be constructed without any bias. In a non-biased embodiment, two or more ultrasound transducers may be placed at known intervals around the circumference of the catheter and directed radially outward from the catheter. Each transducer is then operated in pulse-echo mode, A-mode, or M-mode to detect the round trip time of flight of the ultrasound pulse to calculate the distance between each transducer and the wall of the IVC. Working in conjunction, the time-of-flight measurements made using the two or more transducers at known intervals around the circumference of the catheter can be used to calculate the shape and size of the IVC. If two transducers positioned 180 degrees apart are used, then the size measurement will represent a diameter of the IVC. If three or more transducers are used, the size measurement can represent a cross-sectional area of the IVC.

FIG. 6 shows an embodiment of catheter 600 employing an ultrasound transducer 608 positioned against the wall of the IVC, but has a further distal section of the catheter which is biased back to the opposite wall of the IVC so the transducer is held against one wall by proximal and distal catheter segments biased against the other wall. A device such as shown in FIG. 6 may have a wish-bone shape in a distal segment 612, to further center and stabilize the position of transducer 608 in the IVC. The wishbone shape may be optimized to interact with the naturally oval shape of the IVC to ensure that the catheter assumes an orientation such that the diameter measurement is anterior-posterior. This embodiment may employ a single transducer that may be positioned against the posterior or anterior wall of the IVC, but a catheter with several transducers may also be employed and work well when positioned against any wall in the IVC, and algorithms may be designed to calculate IVC diameter based on the different measurements. For example, in some embodiments, a look-up table and/or correlation calculation may be used to approximate spatial relationships between one or more transducers and/or one or more walls of the IVC. The wishbone-shaped catheter may be designed with no curve 604, so that the wishbone self-orients in a lateral orientation, and at least two transducers 608 are located facing anteriorly and posteriorly, so that in combination they determine the overall anterior-posterior dimension of the IVC.

Another alternative design is shown in FIG. 7. In this embodiment, a catheter 700 has two or more bowed resilient wire or ribbon elements 704 located in a distal catheter section and extending from the sides of the catheter, to engage the vessel wall and thereby help center the catheter within the IVC. Alternatively these resilient elements may be deployed from the distal end of catheter 700, and in some embodiments may be separated axially a substantial distance from any ultrasound transducer so as not to distend the vessel where measurements are to be taken. This separation forms an anchor isolation structure 707. As shown, catheter 700 has an ultrasound emitter/receiver 708 capable of detecting the distance to the vessel walls at multiple points around the circumference of the catheter. For example, the emitter/receiver may comprise several ultrasound transducers, e.g., four or more, distributed around a catheter shaft, each aiming in a different direction radially from the catheter. By measuring the distance to the IVC wall in each direction, the IVC radius, diameter, area, and/or circumference can be calculated. In a further variation, wire or ribbon elements 707 may be provided on only one side of the shaft so the shaft/transducer is positioned against one side of the vessel and measures reflection from the opposite side.

Wire leads from each of the transducers or measuring devices at the distal end of the catheter lead to a connector at the proximal end, which is connected to an electronics box or processing module (see FIG. 14) including a processor, memory and associated hardware and software as required to perform functions such as a) send the appropriate electrical signals to generate ultrasound signals in the transducers; b) measure the reflected ultrasound signal in each of the transducers; c) use algorithms to calculate the IVC diameter, shape, and/or variation in its diameter or shape; and d) display that information in a simple graphical user interface (GUI). The GUI may be provided as a simple display. Among the useful information it might report are the anterior-posterior IVC diameter, the variation in anterior-posterior diameter, the ratio of A-P and lateral diameters, the rate of change of these measurements or the change in these measurements over a time period such as the past hour, or other calculated measurements. Embodiments of the GUI may have alarms if the IVC A-P diameter becomes too low, or is dropping too quickly. It could also be connected via wires or wirelessly to other therapeutic devices, such as an IV pump infusing diuretics, or an IV pump infusing fluid in a patient in shock, or a dialysis or ultrafiltration machine removing fluid.

In further alternative embodiments, sensors may be placed both along the catheter and near the distal end. For example, in some embodiments, at least one oxygen saturation sensor (such as fiberoptics which emit various wavelengths of light, and measure the blood's relative reflectance of those different wavelengths) is placed along in the SVC portion of the catheter, while at least one other oxygen saturation sensor is placed in the IVC portion of the catheter and data from these sensors can be used to track changes in venous oxygen saturation in the SVC versus IVC. Further, pressure sensors can be placed at one or more locations along the catheter to measure pressures in the IVC, SVC, and/or right atrium. Doppler ultrasound sensors could be used to measure blood flow in the IVC and/or the SVC, giving an effective measurement of overall cardiac output as well as the relative IVC and SVC flow rates.

In yet further alternative embodiments, a lumen/channel is provided in the catheter that can be used to either deliver drugs and fluids, as well as be used to withdraw blood. Thus, some embodiments may include a device capable of delivering therapeutic agents (such as drugs or saline) through a lumen, retrieving blood from a lumen, detecting vena cava volume, detecting vena cava pressures, and/or detecting vena cava oxygen saturation, including measuring differences in oxygen saturation of blood in the SVC versus IVC. Other embodiments may include multiple lumens that allow blood to be withdrawn from different portions of the vena cava, such as withdrawing blood samples from the SVC and the IVC without the need for repositioning the device. Such withdrawal of samples from different sites can allow for comparison of venous oxygen saturation from the SVC and IVC using external sensors without the need for embedded oxygen sensors directly in the catheter.

A further exemplary embodiment is shown in FIGS. 8-13. As shown therein, a device 800 made in accordance with this embodiment may comprise four major components or assemblies: an electronics capsule 804, an anchor element 808, an anchor isolation structure 812 connecting the electronics capsule and anchor element and a catheter 816. Electronics capsule 804 comprises a sealed housing 820 for containing control, power and other alternative functional modules and provides a self-contained, sealed device. Alternatively one or more of these functions may be provided externally with communication through the catheter. Capsule 804 also provides support for a transceiver 824, which in the case of the illustrated device is a single ultrasound transceiver positioned at the inferior end of the device. In one embodiment, where all other functions are provided externally with communication through the catheter shaft, capsule 804 serves as a housing for transceiver 824. Transceiver 824 may utilize one or more ultrasound crystals to measure IVC diameter by emitting an ultrasound pulse, and then detecting the reflection of that pulse from the opposing wall of the IVC. Other modes of detection with ultrasound receivers and/or other transceiver types may be alternatively employed by persons of ordinary skill without departing from the teachings of this disclosure. Electronics capsule 804 generally will be provided with the lowest possible profile so as to minimize obstruction of the lumen when positioned in the IVC.

Electronics capsule 804 is connected to anchor element 808 at the superior end of capsule 804. Anchor element 808 as depicted in this embodiment includes a single anchor wire 828 configured in a generally figure-eight or double helix shape. Alternatively, the same or similar configurations can be provided with two or more wires. Anchor wire 828 is pinned to a telescoping deployment member 832 at both its inferior end 836 and superior end 840. The telescoping deployment member includes an inner member 844, which is secured to electronics capsule 804, through anchor isolation structure 812, and an outer member 848. Relative motion between inner member 844 and outer member 848 moves anchor wire 828 from a collapsed position to a deployed or anchoring position.

Various actuation mechanisms may be utilized for deploying and securing anchor element 808. In one alternative, anchor wire 828 is resilient, with shape-memory properties configured to provide a rest state in the deployed configuration. In this alternative, device 800 may be delivered to the desired location in the IVC via a conventional guide catheter like catheter 816 or other suitable sheath type delivery device. When position is confirmed as described below, device 800 is ejected from catheter 816 with anchor element 808 self-deploying upon ejection.

In another alternative deployment mechanism (not shown), an actuating wire provided through the catheter is connected to the deployment member at the superior end. The actuating wire may be permanently attached to facilitate deployment and collapse of the anchor wire, or may releasably be connected using a mechanical release mechanism, for example a screw threaded connection, spring release, hooks or other such means known in the art. The actuating wire may be a single or double wire, which may be coaxial or parallel, depending on the mode of actuation. In this alternative, movement of the actuating wire effects relative movement of inner and outer telescoping deployment members like inner and outer telescoping deployment members 844, 848 to deploy anchor wire like anchor wire 828 from the collapsed configuration to the expanded, deployed configuration as explained above. After deployment of an anchor element like anchor element 808, the actuating wire is released from a device like device 800 according to its mode of connection to leave the device secured in the IVC via the anchor element.

As mentioned above, a further feature of this and other embodiments disclosed herein is the spacing between transceiver 824 position relative to anchor element 808, provided by anchor isolation structure 812. In general, it is preferred that anchor element 808 be positioned sufficiently distant from transceiver 824 so as to not have an effect upon the IVC size or shape at or close to the location of measurement due to the anchoring force imparted to the IVC wall (W). Anchor isolation structure 812 ensures the desired positioning, which may be approximately ½ to 4 times the IVC diameter as indicated above, typically in the range of about 2-6 cm, and in some cases more preferably about 3-5 cm. In general, the IVC has a somewhat oval cross section with a minor axis of the oval extending in the anterior-posterior direction and a major axis extending in the lateral-medial direction. It is thus desirable to minimize any effect of device 800 on this natural oval shape at or close to the point of measurement.

Figure 12:
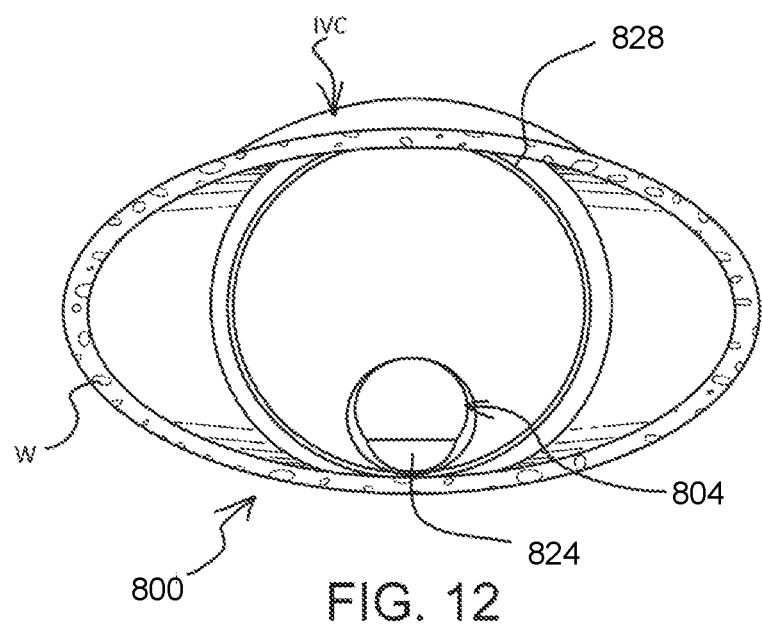
FIG. 12 is an end view of the device of FIG. 8 or 11 from an inferior aspect.
Figure 13:
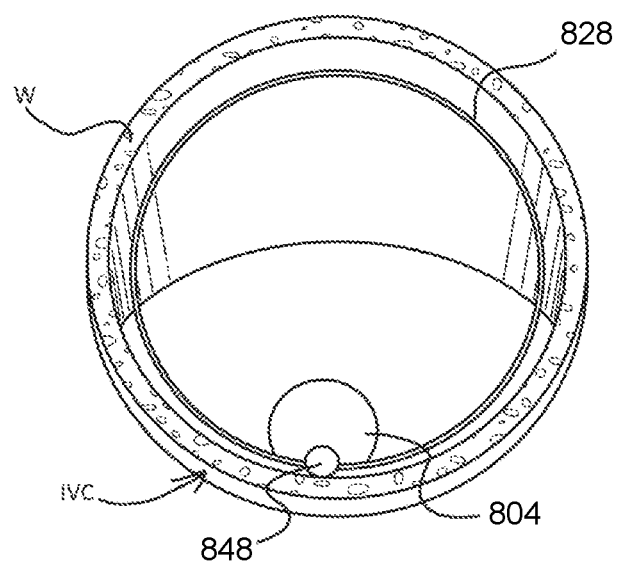
FIG. 13 is an end view of the device of FIG. 8 or 11 from a superior aspect.

The shape of the IVC and possible effect of anchor element 808 on the IVC shape is illustrated, in one possible configuration, in FIGS. 8-13. As shown therein, at the more inferior portion of the IVC, proximate transceiver 824, the IVC assumes its more natural oval shape as best seen in FIG. 12. However, at the superior portion where subjected to the force of anchor wire 828 of anchor element 808, the IVC is forced into a more circular shape as best seen in FIG. 13. Thus, not only does anchor element 808 potentially distort the shape of the IVC, it may also stiffen the IVC so as not to be as responsive to varying fluid volumes which may indicate heart failure risk. Anchor isolation structure 812 reduces or eliminates such problems as might otherwise be associated within sensing devices positioned in the IVC.

In order to achieve accurate measurement with transceiver 824 using an anchor configuration of the type shown in FIGS. 8-13, device 800, from deployment member 832 through anchor isolation structure 812 into electronics capsule 804, should be provided with a stiffness sufficient to maintain the electronics capsule (and transceiver) against the wall (W) of the IVC at one side and yet provide sufficient flexibility (and smoothness) to avoid damage or erosion of the IVC wall by contact with the device over the remaining lifetime of the patient.

As also shown in FIGS. 8-13, it may be most advantageous if the illustrated device, i.e., device 800, or other device disclosed herein, is positioned with an electronics capsule like electronics capsule 804, and more specifically an active transceiver (e.g., ultrasound transceiver) like transceiver 824, against the posterior wall (W) of the IVC so as to measure the distance to the anterior wall. This arrangement may offer advantages in accuracy and sensitivity in measurements by measuring along the minor anterior-posterior axis of the oval IVC shape, and by measuring from the posterior wall, such that bony structures lying behind the posterior wall, which may create artifacts or other interference with ultrasound measurements, may be avoided. Such positioning may provide for the greatest accuracy in measurement of diameter over the respiratory cycle (e.g., measurement of diameter variability vs. static measurement). While a single ultrasound transceiver, i.e., transceiver 824, is shown in FIGS. 8-13, a similar device with more than one ultrasound crystal may be positioned elsewhere in the IVC, for example in the center of the IVC, with two crystals measuring the distance to the anterior and posterior walls simultaneously. Specific requirements for positioning and measurements may be clinically determined based on patient anatomy as determined by the procedure provider, and the device to be implanted, such as device 800, may be modified according to the teachings contained herein to suit those specific patient requirements.

In general, devices as disclosed herein, such as device 800, may be positioned at any suitable position in the IVC based on clinical assessment. In one example, the transceiver of the device, such as an ultrasound crystal, may be disposed at the cranial end of the device, with the cranial end then positioned in the IVC between the renal veins and the hepatic veins. In this case, an anchor element like anchor element 808 may be disposed at the opposite, caudal end of the device and thus positioned in the IVC inferior to the renal veins. Also, when positioning the device on the posterior wall of the IVC, it may be desirable to ensure that the device is centrally located on the posterior wall and oriented with the transceiver facing at least substantially straight across the minor axis for most accurate measurements. Positioning of the device in the IVC may be controlled using conventional catheterization techniques with observation under fluoroscopy. However, in a device like device 800, such as is illustrated, transceiver 824 may be used to assist in confirming placement by slightly rotating electronics capsule 804 so as to effectively scan the opposite IVC walls with an ultrasound sensor of the transceiver to detect placement position relative to the oval IVC cross-sectional shape. The device also may be positioned in the SVC.

As shown in FIGS. 8, 11, 12 and 13, a device like device 800 made in accordance with the present disclosure may be positioned within the IVC (or SVC) such that transceiver 824 is located inferior to the end of catheter 816 relative to electronics capsule 804 with anchor element 808 and/or wire 828 located between the catheter and the electronics capsule. In this embodiment, device 800 is delivered from a superior insertion point such as the jugular vein, using conventional cardiac catheterization techniques. A connector wire 852 may be used to deliver and retrieve device 800. Further functions or treatments as well as communication with device 800 may also be provided through catheter 816 as may be devised by persons of ordinary skill in the art for particular clinical applications based on the teachings contained herein. Alternatively, inferior insertion may be performed, as illustrated in FIG. 9.

Figure 9:
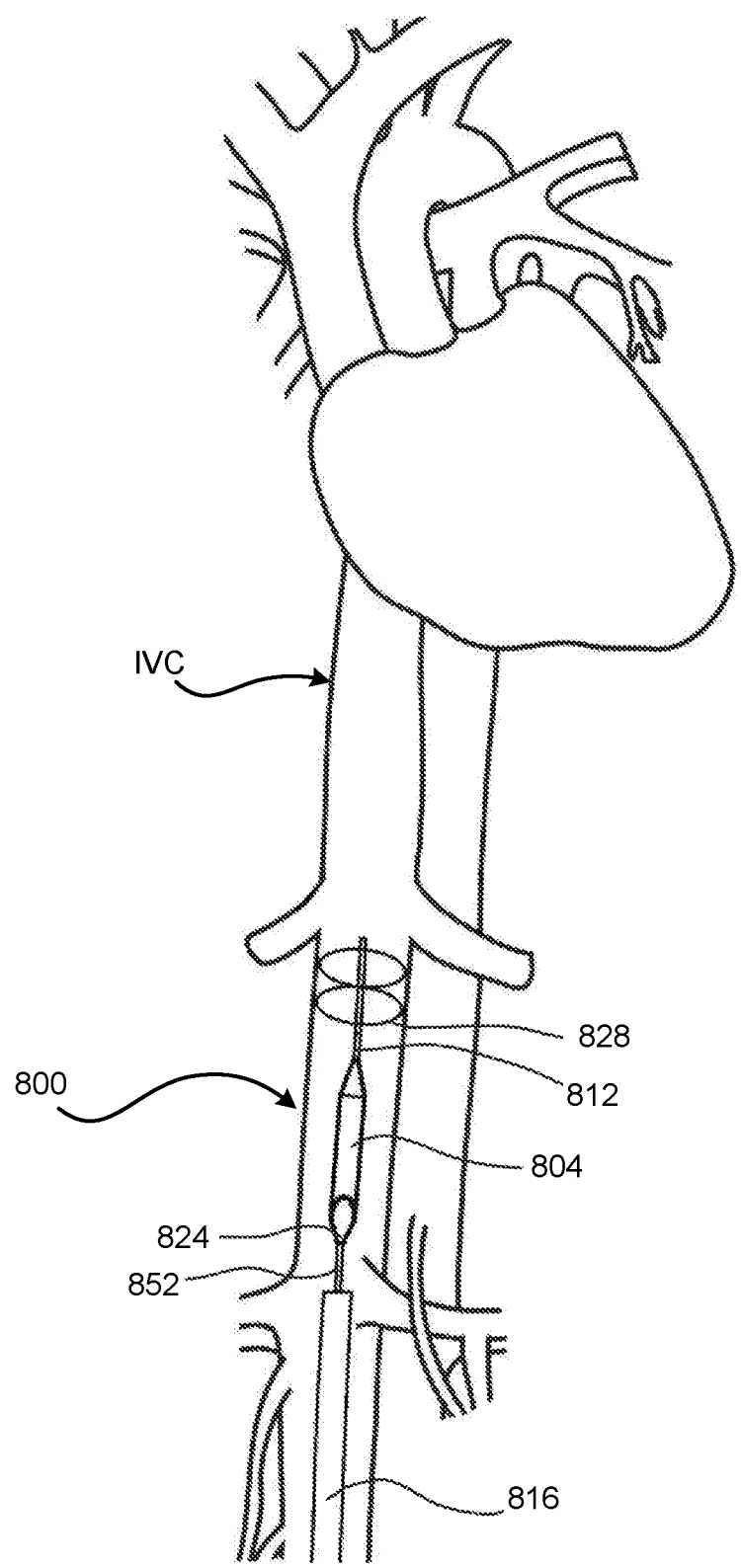
FIG. 9 is a diagram of a device made in accordance with aspects of the present invention that is disposed within the IVC via a catheter inserted via an inferior access site and which does not pass through the superior vena cava.

However, in some embodiments, as shown in FIG. 9, a device like device 800 made in accordance with the present disclosure may be positioned within the IVC such that transceiver 824 is located proximal to the end of catheter 816 relative to electronics capsule 804 with anchor element 808 and/or wire 828 located on the opposite end of the electronics capsule from the catheter. This embodiment may be delivered via conventional femoral vein cardiac catheterization procedures. Alternatively, inferior, femoral vein insertion may be performed using a device like device 800 and other elements as arranged in FIG. 8.

Generally, electronics capsule 804, transceiver 824, anchor element 808 and/or wire 828, and any other elements of a device made in accordance with the present disclosure may be disposed at any position and in any orientation within the IVC provided that device 800 can provide the functionality described herein.

Figure 10:
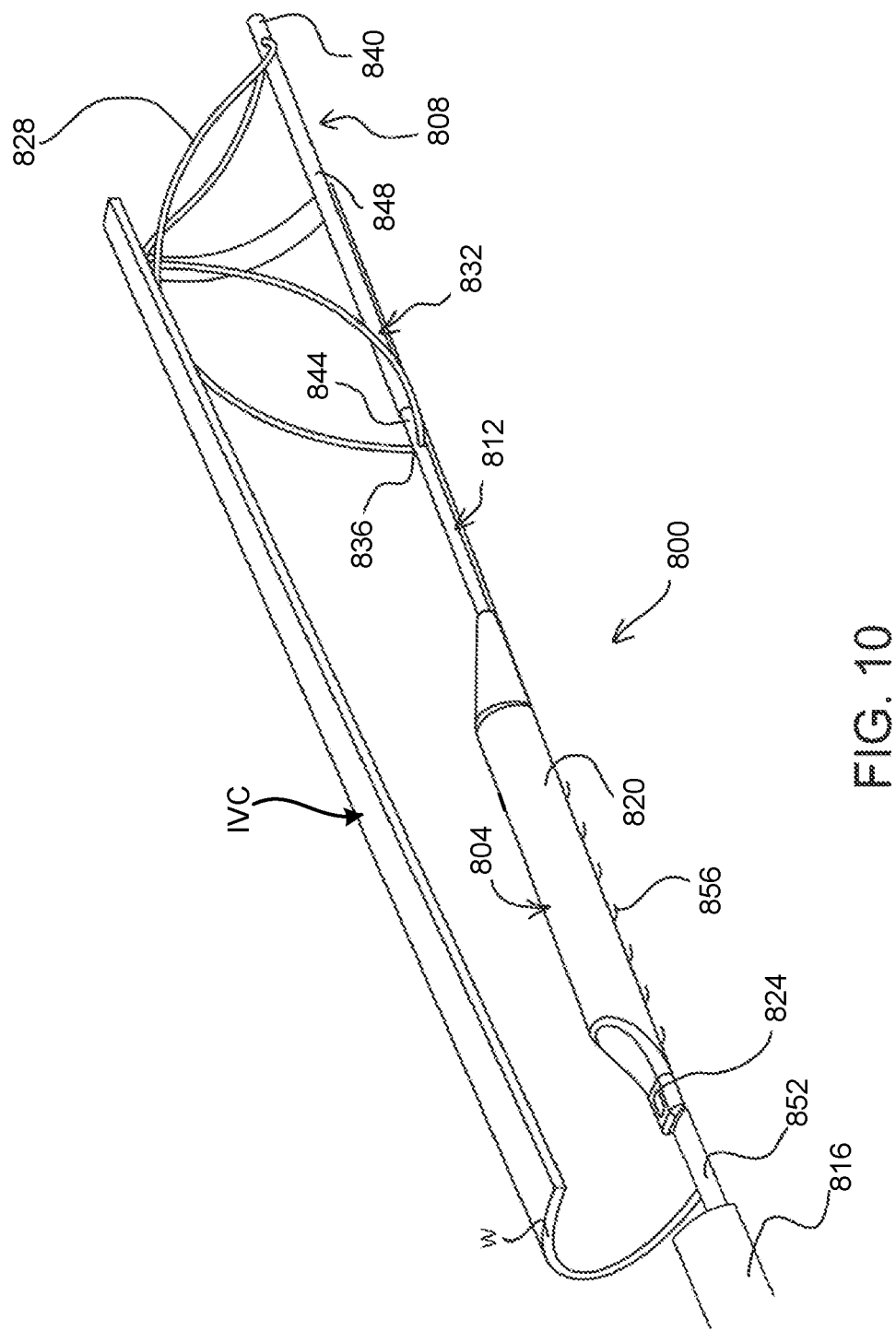
FIG. 10 is a perspective view of a further alternative embodiment positioned in a partially cross-sectioned portion of the IVC.
Figure 11:
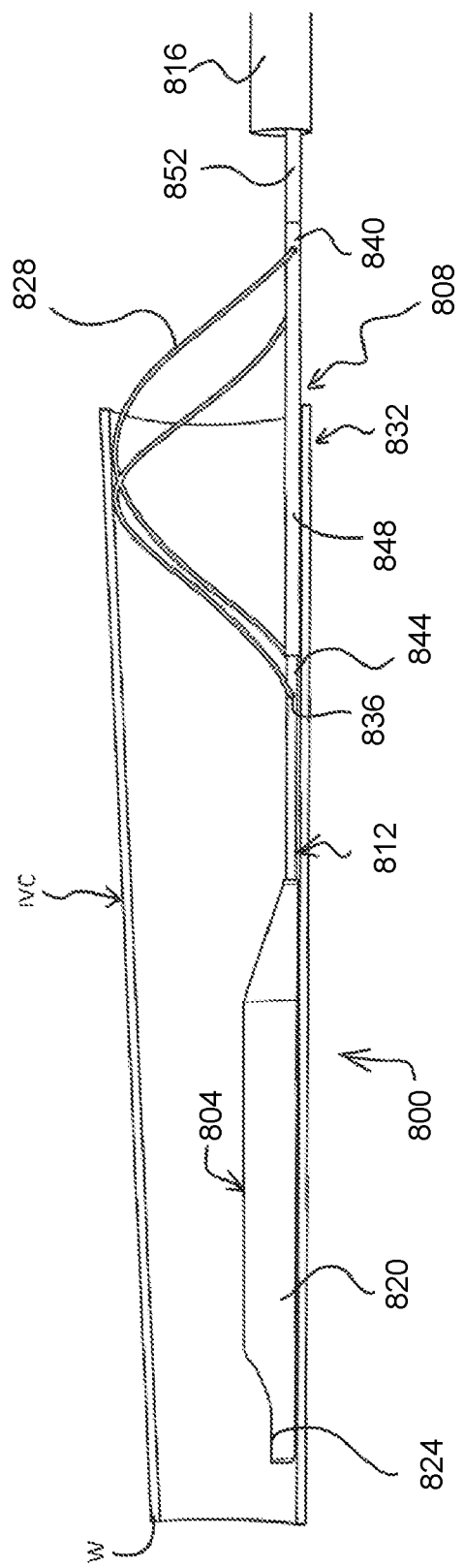
FIG. 11 is a side view of the embodiment shown in FIG. 8 in a partially cross-sectioned IVC.

In a further alternative embodiment, as shown in FIG. 10, additional anchor elements may be provided on electronics capsule 804, such as one or more barbs 856. It is to be noted, however, that while barbs 856 are shown in FIG. 10, they are an optional feature. Basic operation of anchor element 808 is described above. As anchor element 808 opens, it shortens and tends to pull back on electronics capsule 804. Through a linkage between barbs 856 and deployment member 832, the relative movement of those two parts during deployment of anchor element 808 may be used to deploy the barbs from the back of electronics capsule 804. Anchor element 808 and barbs 856 may be positioned to engage the IVC wall (W) in opposition to one another to reinforce anchoring force and security. However, as previously indicated, substantially the same device as device 800 may be alternatively provided without anchor barbs 856, held in place only by the collapsible/expandable double helix anchor wire 828 of anchor element 808. These anchor structures, as well as others described above, are configured to achieve secure fixation against both longitudinal and rotational movement while preferentially maintaining at least transceiver 824 in the posterior aspect of the IVC, most preferably against the posterior IVC wall. The anchor elements described also can be deployed and redeployed multiple times during a placement procedure in order to ensure the most optimum placement of device 800. The shape or configuration of anchor wire 828 also may be adapted for IVC size and shape using different anchor element configurations as will be appreciated by persons of ordinary skill in the art based on the teachings presented herein.

Catheters according to embodiments described herein also may be used in a patient treatment system to monitor and modulate therapy. One such exemplary system 900, schematically illustrated in FIG. 14, may comprise integration of a diagnostic catheter 902 as described above in a closed loop system with an implanted or catheter-based therapeutic device 904, such as a drug delivery device (drug/diuretic pump) or mechanical device (such as a renal pump, IV infusion pump, dialysis system or ultrafiltration system) to manage blood volume. Where catheter 902 employs passive detection elements such as ultrasound reflective elements, external ultrasound transducer 906 may be incorporated. System 900 may utilize IVC measurements as an input/control metric for the system. The diagnostic catheter would detect a high diameter/low collapsibility or low diameter/high collapsibility reading and initiate the therapeutic device to either deliver drug or commence treatment to reduce total blood volume or the impact of the elevated volume, adding fluid to increase blood volume, or initiate or modulate other appropriate therapy. The diagnostic catheter could then be used to manage the rate of treatment to reduce the total time of operation of the therapeutic device. The diagnostic and therapeutic devices could be linked physically or wirelessly. There could also be power transfer between the two devices, through wired or wireless means.

In order to carry out these system functions, in one possible embodiment as shown, diagnostic catheter 902 (and/or external ultrasound transducer 906) communicates with and may be controlled by control module 908. Control module 908 may include one or more processors, memory and other components as may be determined by persons of ordinary skill. GUI 910 also may be incorporated into control module 908 as previously discussed. Control module 908 is provided with a communication and/or power link 912 to therapeutic device control module 914, which also may include one or more processors, memory and other conventional components configured to control therapeutic device 904. GUI 916 may also be provided.

The different design details, individual features and embodiments described above could clearly be "mixed and matched" in different designs and combinations. The optimal designs will be easy and safe for the physician to use, provide accurate and consistent measurements, and be inexpensive to manufacture. Based on the teachings presented herein, persons of ordinary skill will appreciate and understand that use of specific individual features are not necessarily limited to use with the embodiment by which they are exemplified herein. For example, any of the detection elements described herein, active or passive, may be employed in any described catheter embodiment regardless of the specific embodiment used to explain the features in this disclosure.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A catheter for monitoring a vascular lumen dimension, comprising:
    an elongate catheter body having proximal and distal ends, the distal end configured for placement within a patient's vasculature;
    a distal end region configured and dimensioned to engage a wall of the vascular lumen to maintain the position of the distal end region with respect to the vascular lumen wall; and
    at least one detection element configured to detect lumen diameter at a monitoring location disposed in the distal end region of said catheter body;
    wherein said catheter body and distal end region are configured for placement in the vena cava with an anchor element disposed in said distal end region configured to securely position the at least one detection element with respect to the vena cava wall; and
    wherein the anchor element is disposed at a longitudinal distance from the at least one detection element sufficient to isolate the at least one detection element from distortions of the vessel caused by the anchoring element.

2. The catheter of claim 1, wherein said detection element comprises an ultrasound transducer and the anchor element is further configured to contact the ultrasound transducer with the vena cava wall with the ultrasound transducer oriented substantially in the direction of the vena cava wall opposite said transducer.

3. The catheter of claim 1, further characterized in that an anchor isolation structure is positioned in said longitudinal distance between the at least one detection element and the anchor element, wherein the anchor isolation structure comprises a member having sufficient stiffness to maintain the at least one detection element substantially in contact with the IVC wall.

4. The catheter of claim 1, wherein the catheter distal end region is configured for placement in the inferior vena cava (IVC) in engagement with the IVC wall.

5. The catheter of claim 1, wherein the distal end region is configured to naturally orient itself in a predictable orientation relative to the anterior-posterior axis of the vessel.

6. The catheter of claim 1, wherein said detection element comprises an ultrasound transducer.

7. The catheter of claim 1, wherein said distal end region comprises a biased, curved portion configured to engage the lumen wall at two spaced apart locations.

8. The catheter f claim 1, further comprising a pressure sensing port disposed in the distal end region.

9. The catheter of claim 1, further comprising an oxygen saturation sensing port disposed in the distal end region.

10. The catheter of claim 1, further comprising one or more blood flow sensors.

11. The catheter of claim 1, wherein said catheter body comprises at least one lumen configured for delivery or removal of fluid into or out of the vascular lumen.

12. The catheter of claim 1, wherein said distal end region comprises positioning means configured to securely position the at least one detection element within the vascular lumen without affecting the natural dimensions and motion of the vascular lumen at the detecting location.

13. A catheter for monitoring a vascular lumen dimension, comprising:
- an elongate catheter body having proximal and distal ends, the distal end configured for placement within a patient's vasculature;
- a distal end region configured and dimensioned to engage a wall of the vascular lumen to maintain the position of the distal end region with respect to the vascular lumen wall;
- at least one detection element configured to detect lumen diameter at a monitoring location disposed in the distal end region of said catheter body;
- wherein said distal end region comprises a biased, curved portion configured to engage the lumen wall at two spaced apart locations; and
- wherein said detection element comprises an ultrasound transducer disposed in said biased, curved portion at a location configured to be positioned in engagement with the lumen wall with said transducer positioned to direct a signal across the lumen and receive the reflection therefrom.

14. A catheter for monitoring a vascular lumen dimension, comprising:
- an elongate catheter body having proximal and distal ends, the distal end configured for placement within a patient's vasculature;
- a distal end region configured and dimensioned to engage a wall of the vascular lumen to maintain the position of the distal end region with respect to the vascular lumen wall;
- at least one detection element configured to detect lumen diameter at a monitoring location disposed in the distal end region of said catheter body;
- an oxygen saturation sensing port disposed in the distal end region; and a second oxygen saturation sensing port disposed in the catheter body proximal to the distal end region positioned to be located in the superior vena cava when the distal end region is positioned in the inferior vena cava.

* * * * *